US010758490B2

(12) United States Patent
Viladot Petit et al.

(10) Patent No.: US 10,758,490 B2
(45) Date of Patent: *Sep. 1, 2020

(54) NANOCAPSULES CONTAINING MICROEMULSIONS

(71) Applicant: LIPOTEC, S.A., Gava Barcelona (ES)

(72) Inventors: Josep Lluis Viladot Petit, Barcelona (ES); Raquel Delgado Gonzalez, Gava Barcelona (ES); Alfonso Fernandez Botello, Malaga (ES)

(73) Assignee: LIPOTEC, S.A., Gava Barcelona (ES)

( * ) Notice: Subject to any disclaimer, the term of this patent is extended or adjusted under 35 U.S.C. 154(b) by 0 days.

This patent is subject to a terminal disclaimer.

(21) Appl. No.: 13/848,558

(22) Filed: Mar. 21, 2013

(65) Prior Publication Data

US 2013/0216596 A1 Aug. 22, 2013

Related U.S. Application Data

(63) Continuation-in-part of application No. PCT/EP2011/004700, filed on Sep. 20, 2011.

(30) Foreign Application Priority Data

Sep. 21, 2010 (ES) .................... 201031400

(51) Int. Cl.
| | |
|---|---|
| *A61K 9/48* | (2006.01) |
| *A61K 8/11* | (2006.01) |
| *A61K 8/64* | (2006.01) |
| *A61K 47/44* | (2017.01) |
| *B01J 13/10* | (2006.01) |
| *B01J 13/08* | (2006.01) |

(52) U.S. Cl.
CPC .............. *A61K 9/4808* (2013.01); *A61K 8/11* (2013.01); *A61K 8/64* (2013.01); *A61K 47/44* (2013.01); *B01J 13/08* (2013.01); *B01J 13/10* (2013.01); *A61K 2800/412* (2013.01)

(58) Field of Classification Search
CPC . A61K 47/44; A61K 8/11; A61K 8/64; A61K 9/4808; A61K 2800/412; B01J 13/08; B01J 13/10
See application file for complete search history.

(56) References Cited

U.S. PATENT DOCUMENTS

| | | | | |
|---|---|---|---|---|
| 2,800,457 A | * | 7/1957 | Green .................. | A61K 9/5089 101/DIG. 29 |
| 3,539,465 A | * | 11/1970 | Jensen .................. | A01N 25/28 264/4.3 |
| 3,692,690 A | * | 9/1972 | Horger .................. | A61K 9/50 264/4 |
| 4,774,231 A | | 9/1988 | Petitou et al. | |
| 4,975,441 A | | 12/1990 | Gibson | |
| 5,015,470 A | | 5/1991 | Gibson | |
| 5,081,151 A | | 1/1992 | Davis et al. | |
| 5,124,354 A | | 6/1992 | Green | |
| 5,288,502 A | | 2/1994 | McGinity et al. | |
| 5,639,473 A | | 6/1997 | Grinstaff et al. | |
| 5,665,383 A | * | 9/1997 | Grinstaff et al. ............. | 424/450 |
| 6,325,951 B1 | * | 12/2001 | Soper ....................... | B01J 13/02 264/4.3 |
| 6,916,490 B1 | * | 7/2005 | Garver et al. ............... | 424/489 |
| 8,178,125 B2 | | 5/2012 | Wen et al. | |
| 8,741,357 B2 | * | 6/2014 | Lintner et al. ............... | 424/725 |
| 2003/0138557 A1 | * | 7/2003 | Allison ...................... | 427/213.3 |
| 2004/0043078 A1 | * | 3/2004 | Herault ....................... | 424/490 |
| 2004/0151778 A1 | | 8/2004 | Richard et al. | |
| 2007/0292523 A1 | | 12/2007 | Moodley et al. | |
| 2008/0084000 A1 | * | 4/2008 | Forster ......................... | 264/4.3 |
| 2008/0233199 A1 | * | 9/2008 | Kumar et al. ................ | 424/499 |
| 2016/0008291 A1 | * | 1/2016 | Ischakov .................... | B82Y 5/00 424/9.6 |

FOREIGN PATENT DOCUMENTS

| | | |
|---|---|---|
| EP | 0064012 | 11/1982 |
| EP | 0211610 | 2/1987 |
| EP | 0277428 | 8/1988 |
| EP | 0334586 | 9/1989 |
| EP | 0375388 | 6/1990 |
| EP | 0403238 | 12/1990 |
| JP | 05-292899 | 6/1992 |
| JP | 10-131043 | 10/1996 |
| JP | 2004-250804 | 2/2003 |
| JP | 2004-532112 | 10/2004 |
| JP | 2009-084224 | 9/2007 |
| WO | 9307861 | 4/1993 |
| WO | 9418954 | 9/1997 |
| WO | 2006035416 | 4/2006 |

(Continued)

OTHER PUBLICATIONS

Jiang. Micro- and nano-encapsulation and controlled-release of phenolic compounds and other food ingredients, Dissertation submitted to the Graduate School—New Brunswick, Rutgers, Jan. 200, 1-146 p.*
Kruif et al., Complex coacervation of proteins and anionic polysaccharides. Current Opinion in Colloid & Interface Science 9 (2004) 340-349.*
Floury et al. Effect of high-pressure homogenization on droplet size distributions and rheological properties of model oil-in-water emulsions. Innovative Food Science & Emerging Technologies 1 (2000), 127-134.*
Khan et al. Measuring Size, Size Distribution, and Polydispersity of Water-in-Oil Microemulsion Droplets using Fluorescence Correlation Spectroscopy: Comparison to Dynamic Light Scattering. J. Phys. Chem. B 2016, 120, 1008-1020. (Year: 2016).*
Oldfield. Enzymes in Water-in-oil Microemulsions ('Reversed Micelles'): Principles and Applications. Biotechnology and Genetic Engineering Reviews., 1994, vol. 12:255-327. (Year: 1994).*

(Continued)

*Primary Examiner* — Robert A Wax
*Assistant Examiner* — Olga V. Tcherkasskaya
(74) *Attorney, Agent, or Firm* — Ann Skerry; Thoburn Dunlap

(57) ABSTRACT

Delivery system based on polymeric nanocapsules which contain microemulsions, and their use in the preparation of pharmaceutical, cosmetic and/or alimentary compositions.

21 Claims, No Drawings

(56) References Cited

FOREIGN PATENT DOCUMENTS

| WO | 2007106555 | 9/2007 |
|---|---|---|
| WO | 2011116962 | 9/2011 |
| WO | 2011116963 | 9/2011 |

OTHER PUBLICATIONS

International Search Report for PCT/EP2011/004700, Completed by the European Patent Office dated Apr. 4, 2012, 4 Pages.
Gottschalck et al. International Cosmetic Ingredient Dictionary and Handbook, 12th edition 2008, vol. 3, 14 Pages, "Biological Polymers and their Derivatives (Including salts, excluding gums, hydrophilic colloids and derivatives)."
Gallarate et al. Journal of Microencapsulation 2009, vol. 26, No. 5, p. 394-402, "Preparation of solid lipid nanoparticles from W/O/W emulsions: Preliminary studies on insulin encapsulation."
Muller et al. Advanced Drug Delivery Reviews 2002, vol. 54, Suppl.1, p. S131-S155, "Solid lipid nanoparticles (SLN) and nanostructured lipid carriers (NLC) in cosmetic and dermatological preparations."
Schafer-Korting et al. Advanced Drub Delivery Reviews 2007, vol. 59, p. 427-443, "Lipid nanoparticles for improved topical application of drugs for skin diseases."
Fry et al. Analytical Biochemsitry 1978, vol. 90, p. 809-815, "Rapid Separation of Low Molecular Weight Solutes from Liposomes without Dilution."
Malcolm et al. Journal of Controlled Release 2004, vol. 97, p. 313-320, "Controlled release of a model antibacterial drug from a novel self-lubricating silicone biomaterial."
Wissing et al. International Journal of Cosmetic Science 2001, vol. 23, p. 233-243, "A novel sunscreen system based on tocopherol acetate incorporated into solid lipid nanoparticles."
Cosgrove. Colloid Science Principles, methods and applications 2005, 22 Pages, Chapter 5 Julian Eastoe, "Microemulsions."
Xie et al. Colloids and Surfaces B: Biointerfaces 2008, vol. 67, p. 199-204, "Effect of PLGA as a polymeric emulsifier on preparation of hydrophilic protein-loaded solid lipid nanoparticles."
Morel et al. International Journal of Pharmaceutics 1994, vol. 105, p. R1-R3, "Incorporation in liposheres of (D-Trp-6)LHRH".
Wissing et al. J. Cosmet. Sci. Sep./ Oct. 2001, vol. 52, p. 313-324, "Investigations on the occlusive properties of solid lipid nanoparticles (SLN)."
Morel et al. International Journal of Pharmaceutics 1996, vol. 132, p. 259-261, "Thymopentin in solid lipid nanoparticles."
Yu et al. European Journal of Pharmaceutics and Biopharmaceutics 1998, vol. 45, p. 199-203, "Saturable small intestinal drug absorption in humans: modeling and interpretation of cefatrizine data."
Jenning et al. J. Microencapsulation 2001, vol. 18, No. 2, p. 149-158, "Encapsulation of retinoids in solid lipid nanoparticles (SLN)".
Muhlen et al. European Journal of Pharmaceutics and Biopharmaceutics 1998, vol. 45, p. 149-155, "Research Paper, Solid lipid nanoparticels (SLN) for controlled drug delivery—Drug release and release mechanism."

* cited by examiner

NANOCAPSULES CONTAINING MICROEMULSIONS

CROSS-REFERENCE TO RELATED APPLICATIONS

This application IS a Continuation in Part of PCT Application No. PCT/EP2011/004700 filed on 20 Sep. 2011, which claims priority to Spanish Patent Application No. P201031400 filed on 21 Sep. 2010, the disclosures of which are incorporated in their entirety by reference herein.

FIELD OF THE INVENTION

This invention relates to a new delivery system for pharmaceutical, cosmetic and/or alimentary active ingredients based on polymeric nanocapsules which contain microemulsions of water in oil (w/o) and which comprise at least one hydrophilic active ingredient dissolved in the aqueous phase.

BACKGROUND

Solid lipid nanoparticles (SLN) constitute an alternative to other particulate systems for the delivery of active ingredients, such as emulsions, liposomes, micelles, microparticles and/or polymeric nanoparticles. SLN are generated by substituting the liquid lipid in the emulsions for a solid lipid, which means that the SLN are solid at room temperature as well as at body temperature.

The use of SLN as delivery systems enables the use of physiologically acceptable lipids, the possibility of avoiding the use of organic solvents in their preparation, and a wide range of routes of administration, which includes through the skin, orally or intravenously. As well as showing good bioavailability, their principal advantages are:

1. Protection of the active ingredient from chemical degradation. The lipid matrix of SLN can protect labile active ingredients from hydrolysis and/or oxidation, such as tocopherol, retinol and coenzyme Q10 [Gohla, S. et al. *J. MicroencapsuL* 18: 149-158 (2001); Schäfer-Korting, M. et al. *Adv. Drug Del. Rev.* 59: 427-443 (2007)].

2. Based on the composition of the lipid particles, they offer control of the speed of active ingredient release and therefore the possibility of achieving sustained release profiles [Mehnert, W. et al. *Eur. J. Pharm. Biopharm.* 45: 149-155 (1998)].

3. Control of dehydration of the skin due to an occlusive effect [Müller, R. H. et al. *J. Cosm. Sci.* 52: 313-323 (2001)].

4. According to its components they can act as ultraviolet radiation filters [Müller, R. H. et al. *Int. J. Cosm. Sci.* 23: 233-243 (2001)].

A new generation of solid lipid nanoparticles are the nanostructured lipid carriers (NLC). These systems have the same advantages as the SLN, and also minimize or avoid some possible problems associated with SLN, such as the low loading capacity and active ingredient expulsion during storage. In contrast to the at least partially crystalline state of the lipid phase in SLN, NLC show a less organized solid lipid matrix. In the case of NLC, there are both solid and liquid compounds in the matrix, thus the greater disorganization leads to the existence of a greater number of holes with the subsequent increase in the ability to encapsulate active ingredients. For the preparation of NLC, sterically very different molecules of lipids are mixed together, mixtures of solid lipids with liquid lipids or oils [Müller, R. H. et al. *Adv. Drug Deliv. Rev.* 54 (Suppl. 1): S131-S155 (2002)].

The SLN and NLC are from 50 nm to 1000 nm in size and are kept stabilized in an aqueous suspension by surfactants or hydrophilic polymers. The NLC and SLN are very suitable vehicles for releasing active ingredients through the skin. Better epidermal penetration of active ingredients is achieved when they are incorporated into SLN or NLC than when they are applied to the skin in the form of a solution or an emulsion.

The SLN have a solid lipid nucleus which can dissolve lipophilic drugs, which is the more common case for use. However, the possibility of incorporating peptides in lipid particles could constitute a protection of the active ingredient from the proteolytic degradation in the gastrointestinal apparatus. However, there are few references of the use of lipids as matrix materials for formulations of peptides and proteins, due to the hydrophobic nature of the lipid matrix, which makes it more appropriate for incorporating lipophilic active ingredients than hydrophilic proteins. The use of emulsions to incorporate hydrophilic active ingredients such as insulin in SLN is described [Gallarate, M. et al. *J. Microencapsul.* 26: 394-402 (2009)]. In the publication of Gallarate et al. the preparation method of SLN implies the use of organic solvents, a factor which is problematic due to the possible retention of their residues. Gasco et al. incorporate thymopentin pentapeptide in solid lipid nanoparticles by two different methods: the formation of a lipophilic ion-pair with hexadecylphosphate, or by the formation of a multiple emulsion w/o/w dissolving the peptide in the internal aqueous phase [Gasco, M. R. et al. *Int. J. Pharm.* 132: 259-261 (1996)]; this latter method is also used by the same authors to incorporate a polypeptide derived from LHRH in SLN [Gasco, M. R. et al. *Int. J. Pharm.* 105: R1-R3 (1994)]. Zhou et al. describe an increase in the efficiency of encapsulation and the load capacity in the incorporation into SLN of different proteins using PLGA (lactic and glycolic acid copolymer) as an emulsifier [Zhou, W. et al. *Colloids and Surfaces, B: Biointerfaces,* 67: 199-204 (2008)].

The encapsulation of hydrophilic compounds in SLN or NLC presents another problem, as would be the diffusion of the active ingredient within the system towards a medium where it would be more soluble, i.e., towards the aqueous system in which the lipid nanoparticles are in suspension.

Although the SLN and the NLC enable the chemical stability of the incorporated active ingredients to be improved, this stabilization is not complete. Surprisingly, the authors of this invention have found greater stabilization against degradation of cosmetic and/or pharmaceutical active ingredients incorporated into SLN or NLC when the SLN or NLC are polymerically coated [Spanish patent application ES P2010-30431].

The preparation procedures of the SLN and NLC, as well as the delivery system described by the authors in the Spanish patent application ES P2010-30431, implies the exposure of the active ingredient to be encapsulated to the temperatures of the melting points of the lipids in the matrix, which can be very high: over 50° C., and in most cases it is usual to heat the mixtures to about 80-90° C. In case of thermolabile active ingredients, like many biological compounds and others of synthetic origin such as synthetic peptides, this hinders the use of delivery systems based on solid lipids. The hydrophilic compounds can be incorporated into the lipid delivery system in the form of a stable microemulsion, which as well as stabilizing the active ingredient, promotes its bioavailability.

A microemulsion is defined as a system of water, oil and an amphiphile which is an optically isotropic and thermodynamically stable solution. Microemulsions are formed spontaneously. Ordinary emulsions, however, require energy for their formation and are thermodynamically unstable [Eastoe, J. *Microemulsions*, in *"Colloid Science: principles, methods and applications"*, Chapter 5. Ed. T. Cosgrove, John Wiley & Sons, Ltd (2005)].

SUMMARY

This invention proposes a delivery system based on polymeric nanocapsules containing microemulsions of hydrophilic active ingredients, which solves the difficulties presented by the systems described in the prior art. The substitution of solid lipids by liquid lipids inside the nanocapsules avoids the exposure of the thermolabile active ingredients to the high melting temperatures of many of the lipids used in the preparation of SLN and NLC.

The delivery system of this invention allows the nanoencapsulation of thermolabile hydrophilic active ingredients avoiding their degradation during the preparation procedure. Furthermore, the delivery system of this invention enables great stabilization of the active ingredients incorporated, avoids the diffusion of hydrophilic active ingredients in the aqueous suspensions of the nanocapsules, and has a great epidermal penetration ability.

DESCRIPTION OF THE INVENTION

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

This invention provides a solution to the aforementioned problems. In a first aspect, this invention relates to a new delivery system of polymerically coated nanocapsules which contain microemulsions of water in liquid lipids or oils (w/o) and which comprise at least one hydrophilic active ingredient dissolved in the internal aqueous phase.

The nanocapsules of this invention comprise a matrix of liquid lipids or oils and a polymer coating. A w/o microemulsion of at least one hydrophilic active ingredient is incorporated into the lipid matrix. The coating of the nanocapsules constitutes their external part and provides a complete and continuous coating of the inner matrix. The terms liquid lipid and oil are used indistinctly in this invention.

The nanocapsules of this invention contain hydrophilic active ingredients incorporated into their interior. The hydrophilic active ingredients incorporated into the nanocapsules of this invention can be, without restriction, cosmetic, pharmaceutical and/or alimentary active ingredients and/or adjuvants, among others.

The polymeric coating of the nanocapsules of this invention constitutes the external barrier of the nanocapsules; it enables the encapsulation of their components and also provides protection for the active ingredients. This increases their stability against chemical degradation by interaction with other possible components of the composition, by hydrolysis and/or by oxidation due to the presence of oxygen and/or light. Furthermore, in the case of hydrophilic active ingredients such as peptides, it avoids the loss of the active ingredient by diffusion towards the external aqueous phase, as often happens in the aqueous dispersions of SLN or NLC. A greater percutaneous penetration of the active ingredients incorporated into the nanocapsules of the invention with regards to microemulsions, liposomes, SLN and NLC is also achieved.

The preparation procedures of the nanocapsules of this invention comprise two stages: a) preparation of the w/o microemulsion of an aqueous solution of the hydrophilic active ingredient in liquid lipids or oils, and b) encapsulation of the microemulsion by means of a polymeric coating.

For the preparation of the microcapsules of the hydrophilic active ingredients, the mixture of liquid lipids or oils, the active ingredients, surfactants, cosurfactants and/or other excipients is microemulsified with water by stirring. Subsequently, the microemulsion is polymerically coated.

The homogenization methods such as homogenization at high pressure enable smaller particles to be obtained and to use a smaller quantity of surfactants.

In a particular embodiment, the size of the drops of the internal microemulsion ranges between 0.1 nm and 80 nm, preferably between 1 nm and 50 nm, and more preferably between 10 nm and 20 nm.

In another particular embodiment, in the preparation process of the nanocapsules of this invention, the polymeric coating can be made following the usual procedures in the prior art: physical-chemical processes (simple coacervation, complex coacervation, simple or complex coacervation with pH change during cross-linking, evaporation of the solvent) and chemical procedures (interfacial polycondensation). Preferably, the process used for the preparation of the nanocapsules of this invention is coacervation.

When encapsulation is carried out by coacervation, the microemulsion which contains the hydrophilic active ingredient dissolved in its aqueous phase is dispersed in an external aqueous solution or dispersion which contains at least one polymer of the coating and can optionally contain other active ingredients, emulsifiers, polymers and/or other excipients. The process can be carried out in just one stage if a solution of the coacervation agent (simple coacervation) or of another polymer (complex coacervation) is poured under stirring onto the previous w/o/w mixture.

In another particular embodiment, in the formation of the polymeric coating of the nanocapsules of this invention a cross-linking agent is used. The cross-linking agent is selected, for example and not restricted to, from the group formed by aldehydes, glutaraldehyde, formaldehyde, transglutaminases, derivatives of methylenebisacrylamide, N,N-methylenebisacrylamide, N, dihydroxyethylene)bisacrylamide, derivatives of ethylene glycol dimethacrylate, ethylene glycol diacrylate, diethylene glycol diacrylate, tetraethylene glycol diacrylate, ethylene glycol dimethacrylate, diethylene glycol dimethacrylate, triethylene glycol dimethacrylate, sodium tripolyphosphate, N-hydroxysuccinamide esters and/or imidoesters.

In another particular embodiment, complex coacervation can be carried out by increasing the pH once the coacervate has formed and before carrying out cross-linking. That is to say, the pH at which the capsule is cross-linked is greater than the pH of coacervation, which enables smaller capsules to be obtained [Spanish patent application ES P2010-30432].

The nanocapsules of this invention can be collected by the usual techniques, such as filtration, centrifugation, spray-drying and/or lyophilization.

In another particular embodiment, the size of the nanocapsules of this invention oscillates between 10 nm and 5000 nm, preferably between 20 nm and 2000 nm, and more preferably between 50 nm-1000 nm.

The percentage of incorporation of active ingredient into the nanocapsules of this invention is quantitative.

In another particular embodiment, the liquid lipid of the nanocapsules of this invention has a melting point below 4° C., and can be liquid or semi-liquid. The liquid lipid is selected, without restriction, from the group formed by vegetable oils, such as soybean oil, sunflower oil, corn oil, olive oil, palm oil, cottonseed oil, colza oil, peanut oil, coconut oil, castor oil, linseed oil, borage oil, evening primrose oil; marine oils, such as fish oils and algae oils; oils derived from petroleum, such as mineral oil, liquid paraffin and vaseline; short-chain fatty alcohols; medium-chain aliphatic branched fatty alcohols; fatty acid esters with short-chain alcohols, such as isopropyl myristate, isopropyl palmitate and isopropyl stearate and dibutyl adipate; medium-chain triglycerides (MCT) such as capric and caprylic triglycerides (INCI: Capric/caprylic triglycerides) and other oils in the Miglyol® series; $C_{12}$-$C_{16}$ octanoates; fatty alcohol ethers, such as dioctyl ether, and/or mixtures thereof. Certain lipophilic active ingredients can also act as liquid lipid matrices at room temperature, for example and not restricted to, beta-carotene, vitamin E and retinol, and/or mixtures thereof.

In another particular embodiment, the surfactant is selected from the group formed by nonionic surfactants, amphoteric surfactants, anionic surfactants, cationic surfactants and/or mixtures thereof. The nonionic surfactant and/or amphoteric surfactant is selected, without restriction, from the group formed by lecithins, alkyl glycosides with an alkyl group that has from 6 carbon atoms to 24 carbon atoms, alkylmaltosides with an alkyl group that has from 6 carbon atoms to 24 carbon atoms, ethoxylated alkylphenols with an alkyl group that has from 6 carbon atoms to 24 carbon atoms and from 5 ethylene oxide units to 30 ethylene oxide units, alkylphenol polyoxyethylene ethers with an alkyl group that has from 6 to 24 carbon atoms, saturated and unsaturated fatty alcohols with an alkyl group that has from 8 carbon atoms to 24 carbon atoms, poloxamers, polysorbates, fatty acid esters with sugars, sorbitane esters, polyethylene glycol fatty acid esters, castor oil, fatty alcohol and polyoxyethylene ethers, fatty acid alkanolamides, amine oxides, alkyl betaines with an alkyl group that has from 6 carbon atoms to 24 carbon atoms, acyl amido betaines, alkylsulfobetaines with an alkyl group that has from 6 carbon atoms to 24 carbon atoms, glycine derivatives, digitonin, inulin lauryl carbamate and/or mixtures thereof. More preferably, the nonionic surfactant and/or amphoteric surfactant is selected from the group formed by octyl glucoside, decyl glucoside, lauryl glucoside, octyl fructoside, dodecyl maltoside, decyl maltoside, nonoxynol-9, polyethylene glycol p-(1,1,3,3-tetramethylbutyl)phenyl ether, palmityl alcohol, oleyl alcohol, poloxamer 188, poloxamer 407, polysorbate 20, polysorbate 60, polysorbate 80, methyl glucose dioleate, sorbitan monostearate or Span 60, sorbitan monolaurate or Span 20, sorbitan monopalmitate or Span 20, sorbitan olivate, polyethylene glycol 40 stearate, polyethylene glycol 50 stearate, polyethylene glycol 100 stearate, polyoxyethylene stearyl ether, polyoxyethylene lauryl ether, cocamide monoethanolamine, cocamide diethanolamine, cocamide triethanolamine, lauramide diethanolamine, lauramide monoethanolamine, cocamidopropylamine oxide, decyl betaine, dodecyl betaine, tetradecyl betaine, cocoyl betaine, cocamidopropyl betaine, cocamidopropyl hydroxysultaine, N-2-cocoyl amidoethyl hydroxyethylglycinate and N-2-cocoyl amidoethyl hydroxyethyl carboxy glycinate and/or mixtures thereof. The anionic surfactant is selected, without restriction, from the group formed by sulfonates such as alkylbenzene sulfonates, alkyl naphthalene sulfonates, ethoxylated fatty alcohol sulfonates, aliphatic sulfonates, hydroxy alkane sulfonates, alkyl glyceryl sulfonate ethers, perfluorooctane sulfonate; alkyl sulfosuccinates, alkyl sulfoacetates; alkyl sulfates such as sodium and ammonium lauryl sulfate, ethoxylated alkyl sulfates; fatty ester sulfates; ethoxylated fatty alcohol sulfates; alkyl ether sulfates; acyl isocyanates; pentafluorooctanoates; carboxylates; ethoxylated alkylphenols; ethanol ammonium salts; diethanolammonium, methylammonium, dimethylammonium, trimethylammonium; alkyl taurates, acyl or fatty acids; alkyl or acyl sarcosinates; phosphates such as phosphate esters, alkyl phosphates, polyoxyethylene lauryl ether phosphate; glutamates; stearates; biliary acids and their salts, such as glycocholic acid and sodium glycocholate, taurococholic acid and sodium taurocholate, taurodesoxycholate and/or mixtures thereof. The cationic surfactant is selected, without restriction, from the group formed by quaternary ammonium salts, such as cetyl trimethyl ammonium bromide, lauryl trimethyl ammonium chloride, benzyl dimethyl hexadecyl ammonium chloride, distearyl dimethyl ammonium chloride, dilauryl dimethyl ammonium chloride, dimyristyl dimethyl ammonium chloride, cetylpyridinium chloride, benzalkonium chloride, benzethonium chloride, methyl benzetonium chloride and/or mixtures thereof.

In another particular embodiment, the cosurfactant is selected, without restriction, from the group formed by low-molecular-weight alcohols and glycols, such as propanol, isopropanol, butanol and hexanol; long-chain fatty acids, such as octanoic acid and butyric acid; phosphoric acid monoesters; benzyl alcohol; biliary acid salts such as sodium cholate, sodium glycholate, sodium taurocholate, sodium taurodesoxycholate and/or mixtures thereof.

In another particular embodiment, the antiflocculant is selected, without restriction, from the group formed by sodium citrate, sodium pyrophosphate, sodium sorbate, amphoteric surfactants, cationic surfactants and/or mixtures thereof.

In another particular embodiment, the viscosifier is selected, without restriction, from the group formed by cellulose ethers and esters, such as methyl cellulose, hydroxyethyl cellulose, hydroxypropyl cellulose and sodium carboxymethyl cellulose; polyvinyl derivatives, such as polyvinyl alcohol, polyvinylpyrrolidone and polyvinyl acetate; alginates; polyacrylates; xanthans; pectins and/or mixtures thereof.

In another particular embodiment, the polymer of the polymeric coating of the nanocapsules of this invention is selected, without restriction, from the group formed by proteins, polysaccharides, polyesters, polyacrylates, polycyanoacrylates, copolymers and/or mixtures thereof. Preferably, the polymer of the coating of the nanocapsules is selected from the group formed by gelatin, albumin, soy protein, pea protein, broad bean protein, potato protein, wheat protein, whey protein, β-lactoglobulin, caseinates, wheat starch, corn starch, zein, alginates, carrageenans, pectins, arabinogalactans, gum arabic, xanthan gum, mesquite gum, tragacanth gum, galactomannans, guar gum, carob seed gum, chitosan, agar, poly(L-lysine), dextran sulfate sodium, carboxymethyl galactomannan, carboxym ethyl cellulose, methyl cellulose, ethyl cellulose, hydroxypropyl methyl cellulose (HPMC), cellulose nitrate, cellulose acetate butyrate, cellulose acetate phthalate, cellulose hydroxypropyl methyl phthalate, cellulose hydroxypropyl methyl acetate succinate, polyvinyl acetate phthalate, poly(ε-caprolactone), poly(p-dioxanone), poly(δ-valerolactone), poly(β-hydroxybutyrate), poly(β-hydroxybutyrate) and p-hydroxyvalerate copolymers, poly(β-hydroxypropionate), methylacrylic acid copolymers (Eudragit® L and S), dimethylaminoethyl methacrylate copolymers (Eudragit® E), trimethylammonium ethyl methacrylate copolymers (Eudragit® RL and RS), lactic and glycolic acid polymers and copolymers, lactic and glycolic acid polymers and copolymers and polyethylene glycol and mixtures thereof.

Depending on the properties of the polymer used for the polymeric coating of the nanocapsules of this invention, it is possible to increase its specificity. A polymer that provides the polymeric coating with a positive charge enables the bond between the nanocapsules of this invention and hair or textile materials to be stronger. Optionally, the polymer of the coating of the nanocapsules of this invention can be a cationic polymer. The cationic polymer can be a natural or synthetic polymer, for example and not restricted to, cationic derivatives of cellulose, such as quaternized hydroxyethyl cellulose, which can be acquired under the name Polymer JR 400™ by Amerchol; cationic starches; diallyl ammonium and acrylamide salt copolymers; quaternized vinylpyrrolidone/vinylimidazole polymers such as Luviquat™ (BASF); condensation products of polyglycols and amines; polyquaternium polymers and copolymers; polymers called polyquaternium-6, polyquaternium-7, polyquaternium-16, polyquaternium-10 Merquats; polyquaternium-4 copolymers; dicocoylethylhydroxyethylammonium, grafting copolymers with a cellulose skeleton and quaternary ammonium groups; quaternized collagen polypeptides such as laurdimonium hydroxypropyl hydrolyzed collagen (Lamequat™ by Grünau); quaternized wheat polypeptides; polyethylenimine; cationic silicone polymers such as amidomethicone or quaternium-22 silicone; adipic acid and dimethylamino hydroxypropyl diethylenetriamine copolymers (Cartaretin™ by Sandoz); acrylic acid copolymers with dimethyldiallylammonium chloride (Merquat™ 550 by Chemviron); cationic chitin derivatives such as chitosan and its derivatives; condensation products of cationic dihalogen alkylene such as dibromobutane with bisdialkylamines; bis-dimethylamino-1,3-propane; derivatives of cationic guar gum such as guar-hydroxypropyltrimonium, Jaguar™ CBS, Jaguar™ C-17, Jaguar™ C-16 by Celanese; quaternary ammonium salt polymers such as Mirapol™ A-15, Mirapol™ AD-1, Mirapol™ AZ-1 by Miranol; quaternized polysaccharide polymers of natural derivatives such as azarose; cationic proteins selected from gelatin, gum arabic; cationic polymers from the group formed by polyamides, polycyanoacrylates, polylactides, polyglycolides, polyaniline, polypyrrole, polyvinylpyrrolidone, amino silicone polymers and copolymers, polystyrene, polyvinyl alcohol, polystyrene and maleic acid anhydride copolymers, methyl vinyl ether, epoxy resins and styrene and methyl methacrylate copolymers; dimethylamino methacrylate, cationic polyacrylates and polymethacrylates such as Eudragit™ RL 30 D by Röhm; polyamine derivatives optionally substituted by polyethylene glycol derivatives; polyamino acids under pH conditions wherein they are cationic; polyethyleneimine; quaternized derivatives of polyvinylpyrrolidone (PVP) and hydrophilic urethane polymers, as well as any mixture of the aforementioned cationic groups.

Optionally, the polymer of the coating of the nanocapsules of this invention can comprise a plasticizing additive. The plasticizing additive is selected, without restriction, from the group formed by citric acid alkyl esters such as triethyl citrate, tributyl citrate, acetyl tributyl citrate and acetyl triethyl citrate, phthalates such as butyl phthalate and diethyl phthalate, glycerin, sorbitol, maltitol, propylene glycol, polyethylene glycol, glucose, saccharose, lanolin, palmitic acid, oleic acid, stearic acid, fatty acid metal salts such as stearic acid or palmitic acid, sodium stearate, potassium stearate, propylene glycol monostearate, acetylated monoglycerides such as monoacetyl glycerin and glyceryl triacetate or triacetin, glyceryl lecithin, glyceryl monostearate, alkyl sebacates such as dibutyl sebacate or diethyl sebacate, alkyl fumarates, alkyl succinates, medium-chain triglycerides (MCT), castor oil, hydrogenated vegetable oils, waxes and/or mixtures thereof.

Optionally other technical additives of the polymer can be added which improve or facilitate the encapsulation process such as, for example, fluidizers, such as talc, colloidal silicon dioxide, glycerin, polyethylene glycol, glycerin monostearate and/or metal stearate salts.

In the context of this invention, the term hydrophilic refers to substances which are soluble in water, with a solubility greater than 1 g per 100 ml of water at 20° C. In this invention, the terms hydrophilic and hydrosoluble are used indistinctly.

The nature of the hydrophilic cosmetic, pharmaceutical and/or alimentary active ingredient and/or adjuvant can be synthetic or natural, or come from a biotechnological procedure or from a combination of a synthetic procedure and a biotechnological procedure. Preferably, the hydrophilic active ingredient of the nanocapsules of this invention is thermolabile. In the context of this invention, a thermolabile active ingredient is understood to be that which presents a degradation equal or greater to 0.5% after having been subjected to a temperature of 80° C. for two hours.

In a particular embodiment, the hydrophilic cosmetic, pharmaceutical and/or alimentary active ingredient is selected, without restriction, from the group formed by amino acids, peptides, proteins, hydrolyzed proteins, enzymes, hormones, vitamins, mineral salts, sugars, nucleotides, nucleic acids, molecules and extracts of biological and biotechnological origin, vaccines, synthetic or partially synthetic hydrophilic molecules and/or mixtures thereof.

In a particular embodiment, the amino acids, their salts and/or derivatives, as well as the commercial mixtures which contain them, are selected, for example and not restricted to, from the group formed by serine, proline, alanine, glutamate, arginine, glycine, methionine, citrulline, sodium methylglycine diacetate (TRILON® M marketed by BASF), derivatives of amino acids which contain cysteine, in particular N-acetyl cysteine, ergothioneine or S-carboxymethylcysteine, and/or mixtures thereof.

In a particular embodiment, the peptides or the commercial mixtures which contain them are selected, for example and not restricted to, from the group formed by peptides of cosmetic use, such as GHK [INCI: Tripeptide-1], acetyl-glutamyl-methionyl-alanyl-isoleucine, acetyl-arginyl-phenylglycyl-phenylglycine, Bodyfensine™ [INCI: Acetyl Dipeptide-3 Aminohexanoate], Relistase™ [INCI: Acetylarginyltriptophyl Diphenylglycine], acetyl-arginyl-phenylglycyl-valyl-glycine, acetyl-arginyl-phenylglycyl-valyl-phenylglycine, diaminopropionyl-alanyl-asparaginyl-histidine, acetyl-arginyl-asparaginyl-histidyl-citrulline-amide, Aldenine® [INCI: Hydrolyzed Wheat Protein, Hydrolyzed Soy Protein, Tripeptide-1], Decorinyl® [INCI: Tripeptide-10 Citrulline], Serilesine® [INCI: hexapeptide-10], Peptide AC29 [INCI: Acetyl Tripeptide-30 Citrulline], Vilastene™ [INCI: Lysine HCl, Lecithin, Tripeptide-10 Citrulline], dGlyage™ [INCI: Lysine HCl, Lecithin, Tripeptide-9 Citrulline], Eyeseryl® [INCI: Acetyl Tetrapeptide-5], Preventhelia® [INCI: Diaminopropionoyl Tripeptide-33], Argireline® [INCI: Acetyl Hexapeptide-8], SNAP-7 [INCI: Acetyl Heptapeptide-4], SNAP-8 [INCI: Acetyl Octapeptide-3], Leuphasyl® [INCI: Pentapeptide-18], Trylagen® [INCI: *Pseudoalteromonas* Ferment Extract, Hydrolyzed Wheat Protein, Hydrolyzed Soy Protein, Tripeptide-10 Citrulline, Tripeptide-1], Inyline™ [INCI: Acetyl Hexapeptide-30], Melatime™ [INCI: Acetyl Tripeptide-40], Thermostressine™ [INCI: Acetyl Tetrapeptide-22] or Liporeductyl® [INCI: Caffeine, Butcherbroom (Ruscus *Aculeatus*) Root Extract, TEA-Hydroiodide, Carnitine, Ivy (*Hedera Helix*) Extract, Escin, Tripeptide-1] marketed by Lipotec, Matrixyl® [INCI: Palmitoyl Pentapeptide-4], Matrixyl® 3000 [INCI: Palmitoyl Tetrapeptide-7, Palmitoyl Oligopeptide], Dermaxyl® [INCI: Palmitoyl Oligopeptide], Calmosensine™ [INCI: Acetyl Dipeptide-1], Biopeptide CL™ [INCI: Glyceryl Polymethacrylate, Propylene Glycol, Palmitoyl Oligopeptide] or Biopeptide EL™ [INCI: Palmitoyl Oligopeptide] marketed by Sederma, pseudodipeptides, IP 2000 [INCI: Dextran, Trifluoroacetyl Tripeptide-2] marketed by IEB and Atrium, Pepha®-Timp [INCI: Human Oligopeptide-20], ECM-Protect® [INCI: Water (Aqua), Dextran, Tripeptide-2] or Melanostatine®-5 [INCI: Dextran, Nonapeptide-1] marketed by Atrium Innovations, Timp-Peptide [proposed INCI: Acetyl Hexapeptide], Bronzing S.F. [proposed INCI: Butiryl Pentapeptide], BONT-L-Peptide™ [INCI: Palmitoyl Hexapeptide-19] or ECM Moduline™ [proposed INCI: Palm itoyltripeptide] marketed by Infinitec Activos, IP2000™ [INCI: Dextran, Trifluoroacetyl tripeptide-2] marketed by Institut Europeen de Biologie Cellulaire, Syn®-Coll [INCI: Palmitoyl Tripeptide-5] marketed by Pentapharm, Neutrazen™ [INCI: Water, Butylene Glycol, Dextran, Palmitoyl Tripeptide-8], ChroNOline™ [INCI: Caprooyl Tetrapeptide-3] or Thymulen®4 [INCI: Acetyl Tetrapeptide-2] marketed by Atrium Innovations/Unipex Group, Meliprene® [INCI: Dextran, Acetyl Heptapeptide-1] or Melitane® [INCI: Acetyl Hexapeptide-1] marketed by Institut Europeen de Biologie Cellulaire/Unipex Group, Skinasensyl™ [INCI: Acetyl Tetrapeptide-15] marketed by Laboratoires Serobiologiques/Cognis, Vialox® [INCI: Pentapeptide-3], Syn®-Ake® [INCI: Dipeptide Diaminobutyroyl Benzylamide Diacetate], Syn®-Coll [INCI: Palmitoyl Tripeptide-5], Syniorage™ [INCI: Acetyl Tetrapeptide-11], Dermican™ [INCI: Acetyl Tetrapeptide-9] marketed by Laboratoires Serobiologiques/Cognis, Kollaren® [INCI: Tripeptide-1, Dextran] marketed by Institut Europeen de Biologie Cellulaire, Collaxyl® IS [INCI: Hexapeptide-9], Laminixyl IS™ [INCI: Heptapeptide], Quintescine™ IS [INCI: Dipeptide-4], UCPeptide™ V [INCI: Pentapeptide] or AT Peptide™ IS [INCI: Tripeptide-3] marketed by Vincience/ISP, glutathione, carnosine and/or mixtures thereof; and peptides of pharmaceutical use, such as glucagon, leuprolide, goserelin, triptorelin, buserelin, nafarelin, deslorelin, histrelin, avorelin, abarelix, cetrorelix, ganirelix, degarelix, desmopressin, somatostatin and analogues of somatostatin such as octreotide, vapreotide and lanreotide, among others.

In another particular embodiment, the proteins, hydrolyzed protein, enzymes and hormones, as well as the commercial mixtures which contain them, are selected, for example and not restricted to, from the group formed by Elhibin® [INCI: *Glycine Soja* (Soybean) Protein], Preregen® [INCI: *Glycine Soja* (soybean) Protein, Oxido Reductases] or Regu®-Age [INCI: Hydrolyzed Rice Bran Protein, *Glycine Soja* (Soybean) Protein, Oxido Reductases] marketed by Pentapharm/DSM, cadherins, integrins, selectins, hyaluronic acid receptors, immunoglobulins, fibroblast growth factor, connective tissue growth factor, platelet-derived growth factor, vascular endothelial growth factor, epidermal growth factor, insulin-like growth factor, keratinocyte growth factors, colony-stimulating growth factors, transforming growth factor-beta, tumor necrosis factor-alpha, interferons, interleukins, matrix metalloproteinases, receptor protein tyrosine phosphatases, hydrolyzed vegetable proteins such as hydrolyzed wheat protein, hydrolyzed soy protein or hydrolyzed whey protein, Lipeptide® [INCI: Hydrolyzed vegetable protein] by Lipotec, Collalift® [INCI: Hydrolyzed Malt Extract] marketed by Coletica/Engelhard, Colhibin™ [INCI: Hydrolyzed Rice Protein] marketed by Pentapharm, Cytokinol® LS [INCI: Hydrolyzed Casein, Hydrolyzed Yeast Protein, Lysine HCL] marketed by Laboratoires Serobiologiques/Cognis, Liftline® [INCI: Hydrolyzed wheat protein] or Ridulisse C® [Hydrolyzed Soy Protein] marketed by Silab, catalase, superoxide dismutase, lactoperoxidase, glutathione peroxidase, lactoprotein, casein, lactoperoxidase, lysozyme, glycosidases, stratum corneum chymotryptic enzyme or SCCE, proteases such as trypsin, chymotrypsin, sutilain, papain or bromelain, DNA repair enzymes such as photolyase or T4 endonuclease V, lipase, luteinizing hormone (LH), follicle-stimulating hormone (FSH), growth hormone, insulin and/or mixtures thereof.

In another particular embodiment, the vitamins are selected, for example and not restricted to, from the group formed by hydrosoluble vitamins, such as vitamin C, vitamin B1, vitamin B2, vitamin B3, vitamin B5, vitamin B6, vitamin B7, vitamin B9, vitamin B12, carnitine and/or mixtures thereof.

In another particular embodiment, the extracts of biological or biotechnological origin, which can be chemically modified, as well as the commercial mixtures which contain them, are selected, for example and not restricted to, from the group formed by vegetable extracts, marine extracts, cell extracts and extracts produced by microorganisms.

The vegetable extracts are selected from the group formed by hydrosoluble vegetable extracts, for example and not restricted to, hydrosoluble extracts of chamomile, ivy, lemon, *ginseng*, raspberry, Roast amaranth, Rehmannias radix, *gardenia*, carrot, orange, peach, pineapple, gentian, hibiscus flower, walnut leaf, pumpkin, peony, *quinoa*, boldo, rough bindweed, *salvia*, pomegranate, oregano, ginger, marjoram, cranberry, grape, tomato, green tea, black tea, aloe vera (*Aloe barbadensis*), *Saphora japonica, papaya*, pineapple, pumpkin, sweet potato, *Bupleurum chinensis, Cecropia obtusifolia, Celosia cristata, Centella asiatica, Chenopodium quinoa, Chrysanthellum indicum, Citrus aurantium Amara, Coffea arabica, Coleus forskohlii, Commiphora myrrha, Crithmum maritimum, Eugenia caryophyllus, Ginkgo biloba, Hedera helix* (ivy), *Hibiscus sabdariffa, Ilex paraguariensis, Laminaria digitata, Nelumbium speciosum, Paullinia cupana, Peumus boldus, Phyllacantha fibrosa, Prunella vulgaris, Prunus amygdalus Dulcis, Ruscus aculeatus* (Butcherbroom extract), *Sambucus nigra, Spirulina platensis* Algae, *Uncaria tomentosa, Verbena officinalis, Opuntia ficus indica, Salix alba, Lupinus* spp., *Secale cereale, Tussilago farfara, Achillea millefolium, Aradirachta indica, Asmuna japonica, Autocarpus incisus, Bidens pilosa, Broussonetia papyrifera, Chlorella vulgaris, Cimicifuga racemosa, Emblica officinalis, Glycyrrhiza glabra, Glycyrrhiza uralensis, Ilex purpurea, Ligusticum lucidum, Ligusticum wallichii, Mitracarpus scaber, Morinda citrifolia, Morus alba, Morus bombycis, Naringi crenulata, Prunus domesticus, Pseudostellariae radix, Rumex crispus,*

*Rumex occidentalis, Sapindus mukurossi, Saxifragia sarmentosa, Scutellaria Galericulate, Sedum sarmentosum Bunge, Stellaria medica, Triticum Vulgare, Uva ursi, Whitania somnifera, Aristoloquia clematis, Rosa moschata, Echinacea angustifolia, Symphytum officinale, Equisetum arvense, Hypericum perforatum, Mimosa tenuiflora, Persea gratissima, Prunus africanum, Tormentilla erectea, Solanum tuberosum, Rosmarinus officinalis, Vaccinium angustifolium, Macrocystis pyrifera algae, Padina pavonica, Malpighia punicitolia, Cynara scolymus, Gossypium herbaceum, Panicum miliaceum, Morus nigra, Sesamum indicum, Glycine soja, Triticum vulgare, Glycine Max* (soy), malt, flax, red clover, kakkon-to, white lupin, hazelnut, maize, beech tree shoots, *Trifolium pratense* (red clover), *Phormium tenax* (New Zealand flax), *Cinnamommum zeylanicum, Laminaria saccharina, Spiraea ulmaria*, Nettle Root, *Pygeum africanum, Avena Sativa, Arnica montana, Cinchona succirubra, Eugenia caryophyllata, Humulus lupulus, Hypericum perforatum, Mentha piperita, Rosmarinus officinalis, Thymus vulgaricus*, plant extract of the genus *Silybum*, extract of legume seeds, extracts of red algae from the genus *Porphyra*, Phytovityl CO [INCI: Aqua, *Zea Mays* Extract] marketed by Solabia, Micromerol™ [INCI: *Pyrus Malus* Extract] or Heather Extract [INCI: *Calluna Vulgaris* Extract] marketed by Coletica/Engelhard/BASF, Proteasyl® TP LS8657 [INCI: *Pisum Sativum* Extract] marketed by Laboratoires Sérobiologiques/Cognis, Radicaptol® [INCI: Propylene Glycol, Water, *Passiflora Incarnata* Flower Extract, *Ribes Nigrum* (Blackcurrant) Leaf Extract, *Vitis Vinifera* (grape) Leaf Extract] marketed by Solabia or ViaPure™ Boswellia [INCI: Olivanum (Boswellia *Serrata*) Extract] marketed by Soliance, EquiStat [INCI *Pyrus* Malus Fruit Extract, *Glycine Soja* Seed Extract] marketed by Coletica/Engelhard, Litchiderm™ [INCI: Litchi *Chinensis pericarp* extract] or Arganyl™ [INCI: Argania *Spinosa* Leaf Extract] marketed by Laboratoires Sérobiologiques/Cognis, Dakaline® [INCI: *Prunus amygdalus dulcis*, Anogeissus leiocarpus bark extract] marketed by Soliance, Actimp 1.9.3® [INCI: Hydrolyzed Lupine Protein] marketed by Expanscience Laboratorios, Pronalene Refirming HSC [INCI: *Triticum vulgare, Silybum marianum*, Glycine Soy, *Equisetum arvense, Alchemilla vulgaris, Medicago sativa, Raphanus sativus*] or Polyplant® Refirming [INCI: Coneflower, Asiatic Centella, Fucus, Fenugreek] marketed by Provital, Lanablue Dakaline® [INCI: Sorbitol, Algae Extract] marketed by Atrium Innovations, Firmiderm® LS9120 [INCI: Terminalia Catappa Leaf extract, *Sambucus* Negra Flower Extract, PVP, Tannic Acid] marketed by Laboratoires Serobiologiques/Cognis, among others.

Cell extracts and extracts produced by microorganisms, or commercial mixtures which contain them, are selected from the group formed by hydrosoluble cell extracts and hydrosoluble extracts produced by microorganisms, for example and not restricted to, Antarcticine® [INCI: *Pseudoalteromonas* Ferment Extract] and Trylagen® [INCI: *Pseudoalteromonas* Ferment Extract, Hydrolyzed Wheat Protein, Hydrolyzed Soy Protein, Tripeptide-10 Citrulline, Tripeptide-1] marketed by Lipotec, yeast extract, extract of *Saccharomyces cerivisiae* and the product of milk fermentation with *Lactobacillus Bulgaricus*, among others.

The amount of hydrophilic active ingredient contained in the delivery system of this invention ranges between 0.00001% in weight and 50% in weight, preferably between 0.0001% in weight and 40% in weight, and more preferably between 0.001% in weight and 30% in weight.

In another particular embodiment, the nanocapsules of this invention comprise other cosmetic and/or alimentary active ingredients and/or adjuvants of any nature, hydrophobes, hydrophiles and amphiphiles, which can be found inside the nanocapsules in solution or in suspension in the lipid matrix, or in the aqueous phase of the microemulsion. In particular, the cosmetic and/or alimentary active ingredients and/or adjuvants are selected, for example and not restricted to, from the group formed by surfactants, humectants or substances which retain moisture, moisturizers or emollients, agents stimulating healing, coadjuvant healing agents, agents stimulating re-epithelialization, coadjuvant re-epithelialization agents, agents which synthesize dermal or epidermal macromolecules, firming and/or redensifying and/or restructuring agents, cytokine growth factors, agents which act on capillary circulation and/or microcirculation, anti-glycation agents, free radical scavengers and/or anti-atmospheric pollution agents, reactive carbonyl species scavengers, 5α-reductase-inhibiting agents, lysyl- and/or prolyl hydroxylase inhibiting agents, defensin synthesis-stimulating agents, bactericidal agents and/or bacteriostatic agents and/or antimicrobial agents and/or germicidal agents and/or fungicidal agents and/or fungistatic agents and/or germ-inhibiting agents, anti-viral agents, antiparasitic agents, antihistaminic agents, NO-synthase inhibiting agents, desquamating agents or keratolytic agents and/or exfoliating agents, comedolytic agents, anti-psoriasis agents, anti-dandruff agents, anti-inflammatory agents and/or analgesics, anesthetic agents, anti-wrinkle and/or anti-aging agents, cosmetic and/or absorbent and/or body odor masking deodorants, antiperspirant agents, perfuming substances and/or perfumed oils and/or isolated aromatic compounds, anti-oxidizing agents, agents inhibiting vascular permeability, hydrolytic epidermal enzymes, whitening or skin depigmenting agents, agents inhibiting sweat-degrading enzymes, agents capable of filtering UV rays, agents which stimulate or regulate keratinocyte differentiation, anti-itching agents, agents which stimulate or inhibit the synthesis of melanin, propigmenting agents, self-tanning agents, melanocyte proliferation stimulating agent, liquid propellants, vitamins, amino acids, proteins, biopolymers, gelling polymers, skin relaxant agents, agents capable of reducing or treating bags under eyes, agents for the treatment and/or care of sensitive skin, astringent agents, agents regulating sebum production, anti-stretch mark agents, lipolytic agents or agents stimulating lipolysis, venotonic agents, anti-cellulite agents, calming agents, agents acting on cell metabolism, agents to improve dermal-epidermal junction, agents inducing hair growth or hair-loss retardants, body hair growth inhibiting or retardant agents, heat shock protein synthesis stimulating agents, muscle relaxants, muscle contraction inhibitory agents, agents inhibiting acetylcholine receptor clustering, anticholinergic agents, elastase inhibitory agents, matrix metalloproteinase inhibitory agents, chelating agents, vegetable extracts, essential oils, marine extracts, mineral salts, cell extracts, emulsifying agents, agents stimulating the synthesis of lipids and components of the stratum corneum (ceramides, fatty acids, etc.), agents obtained from a bio-fermentation process and/or mixtures thereof. The nature of these active ingredients and/or cosmetic and/or alimentary adjuvants can be synthetic or natural, such as vegetable extracts, or come from a biotechnological process or from a combination of a synthetic process and a biotechnological process. Additional examples can be found in the *CTFA International Cosmetic Ingredient Dictionary & Handbook,* 12th Edition (2008). In the context of this invention, a biotechnological process is understood to be any process which produces the active ingredient, or part of it, in an organism, or in a part of it.

In a particular embodiment, the humectant or substance that retains moisture, moisturizer or emollient is selected, for example and not restricted to, from the group formed by polyols and polyethers such as glycerin, ethylhexylglycerin, caprylyl glycol, pentylene glycol, butylene glycol, propylene glycol and their derivatives, triethylene glycol, polyethylene glycol, Glycereth-26, Sorbeth-30; panthenol; pyroglutamic acid and its salts and derivatives; amino acids, such as serine, proline, alanine, glutamate or arginine; ectoine and its derivatives; N-(2-hydroxyethyl)acetamide; N-lauroyl-pyrrolidone carboxylic acid; N-lauroyl-L-lysine; N-alpha-benzoyl-L-arginine; urea; creatine; α- and β-hydroxy acids such as lactic acid, glycolic acid, malic acid, citric acid or salicylic acid, and their salts; polyglyceryl acrylate; sugars and polysaccharides, such as glucose, saccharide isomerate, sorbitol, pentaerythritol, inositol, xylitol, trehalose and derivatives thereof, sodium glucuronate, carraghenates (*Chondrus crispus*) or chitosan; glycosaminoglycans such as hyaluronic acid and derivatives thereof; aloe vera in any of its forms; honey; soluble collagen; lecithin and phosphatidylcholine; ceramides; cholesterol and its esters; tocopherol and its esters, such as tocopheryl acetate or tocopheryl linoleate; long-chain alcohols such as cetearyl alcohol, stearyl alcohol, cetyl alcohol, oleyl alcohol, isocetyl alcohol or octadecan-2-ol; long-chain alcohol esters such as lauryl lactate, myristyl lactate or $C_{12}$-$C_{15}$ alkyl benzoates; fatty acids such as stearic acid, isostearic acid or palmytic acid; polyunsaturated fatty acids (PUFAs); sorbitans such as sorbitan distearate; glycerides such as glyceryl monoricinoleate, glyceryl monostearate, glyceryl stearate citrate or caprylic and capric acid triglyceride; saccarose esters such as saccarose palmitate or saccarose oleate; butylene glycol esters, such as dicaprylate and dicaprate; fatty acid esters such as isopropyl isostearate, isobutyl palm itate, isocetyl stearate, isopropyl laurate, hexyl laurate, decyl oleate, cetyl palmitate, di-n-butyl sebacate, isopropyl myristate, isopropyl palmitate, isopropyl stearate, butyl stearate, butyl myristate, isopropyl linoleate, 2-ethylhexyl palmitate, 2-ethylhexyl cocoate, decyl oleate, myristyl myristate; squalene; mink oil; lanolin and its derivatives; acetylated lanolin alcohols; silicone derivatives such as cyclomethicone, dimethicone or dimethylpolysiloxane; Antarcticine® [INCI: *Pseudoalteromonas* Ferment Extract] or acetyl-glutamyl-methionyl-alanyl-isoleucine, acetyl-arginyl-phenylglycyl-phenylglycine or acetyl-arginyl-6-aminohexanoyl-alanine marketed by Lipotec, petrolatum; mineral oil; mineral and synthetic waxes; beeswax (cera alba); paraffin; or waxes and oils with vegetable origins such as candelilla wax (*Euphorbia cerifera*), carnauba wax (*Copernicia cerifera*), shea butter (*Butirospermum parkii*), cocoa butter (*Theobroma cacao*), castor oil (*Ricinus communis*), sunflower oil (*Helianthus annuus*), olive oil (*Olea europaea*), coconut oil (*Cocos nucifera*), palm oil (*Elaeis guineensis*), wheat germ oil (*Triticum vulgare*), sweet almond oil (*Prunus amygdalus dulces*), musk rose oil (*Rosa moschata*), soya bean oil (*Glycine soja*), grape seed oil (*Vitis vinifera*), calendula oil (*Calendula officinalis*), jojoba oil (*Simmonsis chinensis*), mango oil (*Mangifera indica*), avocado oil (*Persea gratissima*), and/or mixtures thereof, among others.

Likewise, in another particular embodiment, the agent stimulating healing, coadjuvant healing agent, agent stimulating re-epithelialization and/or coadjuvant re-epithelialization agent is selected, for example and not restricted to, from the group formed by extracts of *Aristoloquia clematis, Centella asiatica, Rosa moschata, Echinacea angustifolia, Symphytum officinale, Equisetum arvense, Hypericum perforatum, Mimosa tenuiflora, Persea gratisima, Prunus africanum, Tormentilla erectea, Aloe vera*, Polyplant® Epithelizing [INCI: *Calendula officinalis, Hypericum perforatum, Chamomilla recutita, Rosmarinus officinalis*] marketed by Provital, Cytokinol® LS 9028 [INCI: Hydrolyzed Casein, Hydrolyzed Yeast Protein, Lysine HCl] marketed by Laboratories Serobiologiques/Cognis or Deliner® [INCI: *Zea May* (Corn) Kernel Extract] marketed by Coletica/Engelhard/BASF, allantoin, cadherins, integrins, selectins, hyaluronic acid receptors, immunoglobulins, fibroblast growth factor, connective tissue growth factor, platelet-derived growth factor, vascular endothelial growth factor, epidermal growth factor, insulin-like growth factor, keratinocyte growth factors, colony-stimulating factors, transforming growth factor beta, tumor necrosis factor alpha, interferons, interleukins, matrix metalloproteinases, receptor protein tyrosine phosphatases, Antarcticine® [INCI: *Pseudoalteromonas* Ferment Extract], Decorinyl® [INCI: Tripeptide-10 Citrulline], Trylagen® [INCI: *Pseudoalteromonas* Ferment Extract, Hydrolyzed Wheat Protein, Hydrolyzed Soy Protein, Tripeptide-10 Citrulline, Tripeptide-1], Bodyfensine™ [INCI: Acetyl Dipeptide-3 Aminohexanoate], marketed by Lipotec, among others.

In a particular embodiment, the agent stimulating dermal or epidermal macromolecular synthesis is selected, for example and not restricted to, from the group formed by agents stimulating collagen synthesis, agents stimulating elastin synthesis, agents stimulating decorin synthesis, agents stimulating laminin synthesis, agents stimulating chaperone synthesis, agents stimulating sirtuin synthesis, agents stimulating hyaluronic acid synthesis, agents stimulating aquaporin synthesis, agents stimulating fibronectin synthesis, agents inhibiting collagen degradation, agents inhibiting elastin degradation, agents inhibiting serine proteases such as leukocyte elastase or cathepsin G, agents stimulating fibroblast proliferation, agents stimulating adipocyte proliferation, agents stimulating adipocyte differentiation, agents stimulating angiogenesis, agents stimulating glycosaminoglycan synthesis, DNA repair agents and/or DNA protecting agents, for example and not restricted to, extracts of *Centella asiatica, Saccharomyces cerevisiae, Solanum tuberosum, Rosmarinus officinalis, Vaccinium angustifolium*, extract of the algae *Macrocystis pyrifera, Padina pavonica*, extract of the plants soy, malt, flax, sage, red clover, kakkon-to, white lupin, hazelnut extract, corn extract, yeast extract, extract of beech tree shoots, extract of leguminosae seeds, extract of plant hormones such as gibberellins, auxins or cytokinins among others, or extract of zooplankton *Salina*, the product of milk fermentation with *Lactobacillus Bulgaricus*, asiaticosides and derivatives thereof, vitamin C and derivatives thereof, cinnamic acid and derivatives thereof, Matrixyl® [INCI: Palmitoyl Pentapeptide-3], Matrixyl® 3000 [INCI: Palmitoyl Tetrapeptide-3, Palmitoyl Oligopeptide] or Biopeptide CL™ [INCI: Glyceryl Polymethacrylate, Propylene Glycol, Palmitoyl Oligopeptide] marketed by Sederma, Antarcticine® [INCI: Pseudalteromonas Ferment Extract], Decorinyl® [INCI: Tripeptide-10 Citrulline], Serilesine® [INCI: Hexapeptide-10], Lipeptide® [INCI: Hydrolyzed vegetable protein], Aldenine® [INCI: Hydrolyzed Wheat Protein, Hydrolyzed Soy Protein, Tripeptide-1], Peptide AC29™ [INCI: Acetyl Tripeptide-30 Citrulline] marketed by Lipotec, Drieline® PF [INCI: Yeast Betaglucan] marketed by Alban Muller, Phytovityl C® [INCI: Aqua, *Zea Mays* Extract] marketed by Solabia, Collalift® [INCI: Hydrolyzed Malt Extract] marketed by Coletica/Engelhard, Phytocohesine® PSP [proposed INCI: Sodium Beta-Sitosterol Sulfate] marketed by Seporga, minerals such as calcium among others, retinoids and derivatives thereof, isoflavonoids, carotenoids, in particular lycopene, pseudodipeptides, retinoids and derivatives thereof such as retinol or retinyl palmitate among others, or heparinoids among others.

In a particular embodiment, the agent inhibiting elastin degradation is selected, for example and not restricted to, from the group formed by Elhibin® [INCI: *Glycine Soja* (Soybean) Protein], Preregen® [INCI: *Glycine Soja* (soybean) Protein, Oxido Reductases] or Regu®-Age [INCI: Hydrolyzed Rice Bran Protein, *Glycine Soja* (Soybean) Protein, Oxido Reductases] marketed by Pentapharm/DSM, Juvenesce™ [INCI: Ethoxydiglicol and caprylic Triglyceride, Retinol, Ursolic Acid, Phytonadione, Ilomastat], Micromerol™ [INCI: *Pyrus* Malus Extract], Heather Extract [INCI: *Calluna Vulgaris* Extract], Extracellium® [INCI: Hydrolyzed Potato Protein] or Flavagrum™ PEG [INCI: PEG-6 Isostearate, Hesperetin Laurate] marketed by Coletica/Engelhard/BASF, Proteasyl® TP LS8657 [INCI: *Pisum Sativum* Extract] marketed by Laboratoires Serobiologiques/Cognis, Relistase™ [INCI: Acetylarginyltriptophyl Diphenylglycine] marketed by Lipotec, Sepilift™ DPHP [INCI: Dipalmitoyl hydroxyproline] marketed by SEPPIC, Vitaderm® [INCI: Alcohol, Water, Glycerin, Hydrolyzed Rice Protein, *Ilex Aquifolium* Extract, Sodium Ursolate, Sodium Oleanolate] marketed by Rahn, Gatuline® Age Defense 2 [INCI: *Juglans Regia* (Walnut) Seed Extract] marketed by Gattefosse, IP2000™ [INCI: Dextran, Trifluoroacetyl Tripeptide-2] marketed by IEB and Atrium, Radicaptol® [INCI: Propylene Glycol, Water, *Passiflora Incamata* Flower Extract, *Ribes Nigrum* (Blackcurrant) Leaf Extract, *Vitis Vinifera* (grape) Leaf Extract] marketed by Solabia or ViaPure™ Boswellia [INCI: Olivanum (Boswellia *Serrata*) Extract] marketed by Soliance, among others.

In a particular embodiment, the matrix metalloproteinase-inhibiting agent is selected, for example and not restricted to, from the group formed by ursolic acid, isoflavones such as genistein, quercetin, carotenoids, lycopene, soy extract, cranberry extract, rosemary extract, *Trifolium* pretense (red clover) extract, *Phormium tenax* (New Zealand flax) extract, kakkon-to extract, sage extract, retinol and derivatives thereof, retinoic acid and derivatives thereof, sapogenins such as diosgenin, hecogenin, smilagenin, sarsapogenin, tigogenin, yamogenin and yucagenin among others, Collalift® [INCI: Hydrolyzed Malt Extract], Juvenesce™ [INCI: Ethoxydiglicol and Caprylic Triglyceride, Retinol, Ursolic Acid, Phytonadione, Ilomastat] or EquiStat [INCI *Pyrus* Malus Fruit Extract, *Glycine Soja* Seed Extract] marketed by Coletica/Engelhard, Pepha®-Timp [INCI: Human Oligopeptide-20], Regu®-Age [INCI: Hydrolyzed Rice Bran Protein, *Glycine Soja* Protein, Oxido Reductases] or Colihibin™ [INCI: Hydrolyzed Rice Protein] marketed by Pentapharm, Lipeptide® [INCI: Hydrolyzed vegetable protein], Peptide AC29 [INCI: Acetyl Tripeptide-30 Citrulline], acetyl-arginyl-asparaginyl-histidyl-citruline-amide marketed by Lipotec, Litchiderm™ [INCI: Litchi *Chinensis* pericarp extract] or Arganyl™ [INCI: Argania *Spinosa* Leaf Extract] marketed by Laboratories Serobiologiques/Cognis, MDI Complex® [INCI: glycosaminoglycans] or ECM-Protect® [INCI: Water (Aqua), Dextran, Tripeptide-2] marketed by Atrium Innovations, Dakaline® [INCI: *Prunus* amygdalus *dulcis*, Anogeissus leiocarpus bark extract] marketed by Soliance, Homeostatine™ [INCI: Enteromorpha *compressa*, *Caesalpinia Spinosa*] marketed by Provital, Timp-Peptide™ [proposed INCI: Acetyl Hexapeptide] or ECM Moduline™ [proposed INCI: Palmitoyltripeptide] marketed by Infinitec Activos, IP2000™ [INCI: Dextran, Trifluoroacetyl tripeptide-2] marketed by Institut Europeen de Biologie Cellulaire, Actimp 1.9.3® [INCI: Hydrolyzed Lupine Protein] marketed by Expanscience Laboratories, Vitaderm® [INCI: Alcohol, Water (Aqua), Glycerin, Hydrolyzed Rice Protein, *Ilex Aquifolium* Extract, Sodium Ursolate, Sodium Oleanolate] marketed by Rahn, adapalene, tetracyclines and derivatives thereof such as minocycline, rolitetracycline, chlortetracycline, metacycline, oxytetracycline, doxycycline, demeclocycline and their salts, Batimastat [BB94; [4-(N-hydroxyamino)-2R-isobutyl-3S-(thiophene-2-ylthiomethyl) succinyl]-L-phenylalanine-N-methylamide], Marimastat [BB2516; [2S—[N4(R"),2R",3S]]—N4[2,2-dimethyl-1-[methylaminocarbonyl]propyl]-N1,2-dihydroxy-3-(2-methylpropyl)butanediamide], among others.

In a particular embodiment, the firming and/or redensifying and/or restructuring agent is selected, for example and not restricted to, from the group formed by extracts of *Malpighia punicitolia, Cynara scolymus, Gossypium herbaceum, Aloe Barbadensis, Panicum miliaceum, Morus nigra, Sesamum indicum, Glycine soja, Triticum vulgare*, Pronalen® Refirming HSC [INCI: *Triticum vulgare, Silybum marianum*, Glycine Soy, *Equisetum arvense, Alchemilla vulgaris, Medicago sativa, Raphanus sativus*] or Polyplant® Refirming [INCI: Coneflower, Asiatic Centella, Fucus, Fenugreek] marketed by Provital, Lanablue® [INCI: Sorbitol, Algae Extract] marketed by Atrium Innovations, Pepha®-Nutrix [INCI: Natural Nutrition Factor] marketed by Pentapharm, or vegetable extracts which contain isoflavones, Biopeptide EL™ [INCI: Palmitoyl Oligopeptide], Biopeptide CL™ [INCI: Palmitoyl Oligopeptide], [INCI: Water (Aqua), Propylene Glycol, Lecithin, Caffeine, Palmitoyl Carnitine], Matrixyl® [INCI: Palmitoyl Pentapeptide-3], Matrixyl® 3000 [INCI: Palmitoyl Tetrapeptide-3, Palmitoyl Oligopeptide] or Bio-Busty™ [INCI: Glyceryl Polymethacrylate, Rahnella Soy Protein Ferment, Water (Aqua), Propylene Glycol, Glycerin, PEG-8, Palmitoyl Oligopeptide] marketed by Sederma, Dermosaccharides® HC [INCI: Glycerin, Water (Aqua), Glycosaminoglycans, Glycogen], Aglycal® [INCI: Mannitol, Cyclodextrin, Glycogen, Aratostaphylos Uva *Ursi* Leaf Extract], Cytokinol® LS [INCI: Hydrolyzed Casein, Hydrolyzed Yeast Protein, Lysine HCl] or Firmiderm® LS9120 [INCI: Terminalia Catappa Leaf extract, *Sambucus* Negra Flower Extract, PVP, Tannic Acid] marketed by Laboratoires Serobiologiques/Cognis, Liftline® [INCI: Hydrolyzed wheat protein], Raffermine® [INCI: Hydrolyzed Soy Flour] or Ridulisse C® [Hydrolyzed Soy Protein] marketed by Silab, Serilesine® [INCI: hexapeptide-10], Decorinyl™ [INCI: Tripeptide-10 Citrulline], Trylagen® [INCI: *Pseudoalteromonas* Ferment Extract, Hydrolyzed Wheat Protein, Hydrolyzed Soy Protein, Tripeptide-10 Citrulline, Tripeptide-1], marketed by Lipotec, Ursolisome® [INCI: Lecithin, Ursolic Acid, Atelocollagen, Xanthan Gum, Sodium Chondroitin Sulfate] or Collalift® [INCI: Hydrolyzed Malt Extract] marketed by Coletica/Engelhard, Syn®-Coll [INCI: Palmitoyl Tripeptide-5] marketed by Pentapharm, Hydriame® [INCI: Water (Aqua), Glycosaminoglycans, *Sclerotium* Gum] marketed by Atrium Innovations or IP2000™ [INCI: Dextran, Trifluoroacetyl tripeptide-2] marketed by Institut Europeen de Biologie Cellulaire among others.

In a particular embodiment, the anti-glycation agent is selected, for example and not restricted to, from the group formed by *Vaccinium angustifolium* extracts, ergothioneine and derivatives thereof, lysine, Aldenine® [INCI: Hydrolyzed Wheat Protein, Hydrolyzed Soy Protein, Tripeptide-1], Vilastene™ [INCI: Lysine HCl, Lecithin, Tripeptide-10 Citrulline], dGlyage™ [INCI: Lysine HCl, Lecithin, Tripeptide-9 Citrulline] or Eyeseryl® [INCI: Acetyl Tetrapeptide-5] marketed by Lipotec, hydroxystilbenes and derivatives thereof, resveratrol or 3,3',5,5'-tetrahydroxystilbene among others.

In a particular embodiment, the free radical scavenger and/or anti-atmospheric pollution agent, and/or the reactive carbonyl species scavenger is selected, for example and not restricted to, from the group formed by tea extract, olive leaf extract, extract of *Rosmarinus officinalis* or extract of *Eichhornia crassipes*, benzopyrenes, vitamin C and derivatives thereof, vitamin E and derivatives thereof, in particular tocopheryl acetate, ascorbyl glycoside, phenols and polyphenols, in particular tannins, tannic acid and ellagic acid, gallocatechol, anthocyanins, chlorogenic acid, stilbenes, indoles, cysteine-containing amino acid derivatives, in particular N-acetylcysteine, ergothioneine, S-carboxymethylcysteine, chelating agents, in particular EDTA or ethylenediamines, carotenoids, bioflavonoids, ubiquinone, idebenone, catalase, superoxide dismutase, lactoperoxidase, glutathione peroxidase, glutathione, benzylidene camphor, pidolates, lignans, melatonin, oryzanol, carnosine and derivatives thereof, GHK [INCI: Tripeptide-1] and its salts and/or derivatives, Aldenine® [INCI: Hydrolyzed wheat protein, hydrolyzed soy protein, tripeptide-1], Preventhelia® [INCI: Diaminopropionoyl Tripeptide-33], diaminopropionyl-alanyl-asparaginyl-histidine or Lipochroman-6 [INCI: Dimethylmethoxy Chromanol] marketed by Lipotec, among others.

In a particular embodiment, the 5α-reductase inhibiting agent is selected, for example and not restricted to, from the group formed by extract of *Cinnamommum zeylanicum, Laminaria saccharina, Spiraea ulmaria, Nettle Root, Pygeum africanum, Avena Sativa, Serenoa repens*, extracts of the plants *Arnica montana, Cinchona succirubra, Eugenia caryophyllata, Humulus lupulus, Hypericum perforatum, Mentha piperita, Rosmarinus officinalis, Salvia officinalis, Thymus vulgaricus*, extract of plants of the genus *Silybum*, extract of plants which contain sapogenins and in particular extract of plants of the genus *Dioscorea*, phytosterols, retinoids and in particular retinol, sulfur and derivatives thereof, zinc salts and in particular lactate, gluconate, pidolate, carboxylate, salicylate or zinc cysteate, selenium chloride, vitamin B6, pyridoxine, capryloyl glycine, sarcosine, finasteride, dutasteride, izonsteride, turosteride and their salts, among others.

Likewise, in another particular embodiment, the lysyl- and/or prolyl-hydroxylase-inhibiting agent is selected, for example and not restricted to, from the group formed by 2,4-diaminopyrimidine 3-oxide or 2,4-diamino-6-piperidinopyrimidine 3-oxide, among others.

In another particular embodiment, the defensin synthesis-stimulating agent is selected, for example and not restricted to, from the group formed by extracts of or hydrolyzed *Aloe Vera, Roast amaranth, Rehmannias radix, arnica, gardenia*, carrot, orange, peach, pineapple, mint, gentian, hibiscus flower, walnut tree leaf, calabaza, peony, *quinoa*, boldo, rough bindweed, sunflower, elderberry, seaweed, hydrolyzed corn, hydrolyzed soy, hydrolyzed rice, valine and its isomers and derivatives, calcium and its salts, α-MSH and fragments contained in the amino acid sequence of α-MSH, vitamin A and its derivatives and precursors, vitamin D3 and its derivatives, jasmonic acid, fumaric acid, malic acid, citric acid, ascorbic acid, lactic acid, acetic acid, adipic acid, tartaric acid, cinnamic acid, glutamic acid, succinic acid, inulin, alkyl glucosides, poly-D-glutamic acid, glycine, L-methionine, L-alanine, L-citrulline, lactoprotein, casein, lactoperoxidase, lysozyme, polyphenol, alkyl glucosides, *Lactobacillus* extract, fusobacteria extracts or non-photosynthetic and non-fruiting filamentous bacteria and Bodyfensine™ [INCI: Acetyl Dipeptide-3 Aminohexanoate] marketed by Lipotec, among others.

In another particular embodiment, the bactericidal and/or bacteriostatic agent and/or antimicrobial and/or germicidal agent and/or fungicidal agent and/or fungistatic agent and/or germ inhibiting agent is selected, for example and not restricted to, from the group formed by macrolides, pyranosides, calcium channel blockers, for example and not restricted to, cinnarizine and diltiazem; hormones, for example and not restricted to, estril, analogues thereof or thyroxine and/or its salts, caprylyl glycol, imidazolidinyl urea, methyl 4-hydroxybenzoate [INCI: methylparaben], ethyl 4-hydroxybenzoate [INCI: ethylparaben], propyl 4-hydroxybenzoate [INCI: propylparaben], butyl 4-hydroxybenzoate [INCI: butylparaben], isobutyl 4-hydroxybenzoate [INCI: isobutylparaben], 1,3-bis(hydroxymethyl)-5,5-dimethylimidazolidine-2,4-dione [INCI: DMDM Hydantoin], benzyl 4-hydroxybenzoate [INCI: benzylparaben], benzyl alcohol, dehydroacetic acid, benzoic acid, sorbic acid, salicylic acid, formic acid, propionic acid, 2-bromo-2-nitropropane-1,3-diol, 3-p-chlorophenoxy-1,2-propanodiol [INCI: chlorphenesin], dichlorobenzyl alcohol, iodopropynyl butylcarbamate, benzalkonium chloride, odor-absorbing fungicides such as zinc ricinoleate, cyclodextrins, benzethonium chloride, chlorhexidine, ethanol, propanol, 1,3-butanediol, 1,2-propylene glycol, undecylenic acid, dehydroacetic acid, N-methylmorpholine acetonitrile (MMA), isopropanol, methanol, 1,2-hexanediol, 1,2-octanediol, pentylene glycol, glycerin laurate, glycerin caprilate, glycerin caprate, benzoyl peroxide, chlorhexidine gluconate, triclosan and derivatives thereof, phenoxyethanol, terpinen-4-ol, α-terpineol, resorcinol, stiemycin, erythromycin, neomycin, clindamycin and its esters, tetracyclines, metronidazole, azelaic acid, tolnaftate, nystatin, clotrimazole, ketoconazole, derivatives of zinc such as zinc piritonate or trithionate, zinc oxide and zinc undecylenate, piroctone olamine, isothiazolinones, selenium sulfur, benzyl hemiformal, boric acid, sodium borate, 6,6-dibromo-4,4-dichloro-2,2'-methylenediphenol [INCI: bromochlorophene], 5-bromo-5-nitro-1,3-dioxane, tosylchloramide sodium [INCI: chloramine T], chloroacetamide, p-chloro-m-cresol, 2-benzyl-4-chlorophenol [INCI: chlorophene], dimethyl oxazolidine, dodecyl dimethyl-2-phenoxyethyl ammonium bromide [INCI: domiphen bromide], 7-ethyl bicyclooxazolidine, hexetidine, glutaraldehyde, N-(4-chlorophenyl)-N-[4-chloro-3-(trifluoromethyl)phenyl]-urea [INCI: cloflucarban], 2-hydroxy-4-isopropyl-2,4,6-cycloheptatriene-1-one [INCI: Hinokitiol], isopropylmethylphenol, mercury salts, aluminum salts, nisin, phenoxyisopropanol, o-phenylphenol, 3-heptyl-2-[(3-heptyl-4-methyl-3H-thiazole-2-ylidene)methyl]-4-methylthiazole iodide [INCI: Quaternium-73], silver chloride, sodium iodide, thymol, undecylenic acid, diethylenetriaminepentaacetic acid, ethylenediaminetetraacetic acid and ethylenediaminetetraacetates, lactoperoxidase, glucose oxidase, lactoferrin, alkylaryl sulfonates, halogenated phenols, phenol mercury acetate and/or mixtures thereof, benzamidines, isothiazolines, derivatives of phthalimide, derivatives of pyridine, guanidines, quinolines, 1,2-dibromo-2,4-dicyanobutane, iodine-2-propylbutyl carbamate, iodine, tamed iodines, peroxo compounds, 4-chloro-3,5-dimethylphenol, 2,2'-methylene-bis(6-bromo-4-chlorophenol), 3-methyl-4-(1-methylethyl)phenol, 3-(4-chlorophenoxy)-1,2-propanediol, 3,4,4'-trichlorocarbanilide (TTC), thiamine essence, eugenol, farnesol, glycerin monolaurate, diglycerin monocaprinate, N-alkyl salicylic acid amides such as n-octyl salicylic acid amide or n-decyl salicylic acid amide, derivatives of halogenated xylene and cresol, such as p-chloro-meta-cresol or p-chloro-meta-xylene, extracts of *Allium sativum, Calendula officinalis, Chamomilla recutita, Echinacea* Purpura, *Hyssopus Officinalis, Melaleuca* altemifolia or tea tree oil, carnation essence, menthol and mint essence, among others.

Likewise, in another particular embodiment, the NO-synthase-inhibiting agent is selected, for example and not restricted to, from the group formed by extracts of the plants *Vitis vinifera, Olea europaea* or *Gingko biloba* among others.

In a particular embodiment, the desquamating agent and/or keratolytic agent and/or exfoliating agent is selected, for example and not restricted to, from the group formed by hydroxy acids and derivatives thereof, β-hydroxyacids, in particular salicylic acid and derivatives thereof, or gentisic acid; α-hydroxyacids and its salts, such as glycolic acid, ammonium glycolate, lactic acid, 2-hydroxyoctanoic acid, α-hydroxycaprylic acid, mandelic acid, citric acid, malic acid or tartaric acid; α- and β-hydroxybutyric acids; polyhydroxy acids such as gluconic acid, glucuronic acid or saccharic acid; keto acids such as pyruvic acid, glyoxylic acid; pyrrolidinecarboxylic acid; cysteic acid and derivatives; aldobionic acids; azelaic acid and derivatives thereof such as azeloyl diglycinate; ascorbic acid and derivatives thereof such as 6-O-palmitoylascorbic acid, ascorbyl glucoside, dipalmitoylascorbic acid, magnesium salt of ascorbic acid-2-phosphate (MAP), sodium salt of ascorbic acid-2-phosphate (NAP), ascorbyl tetraisopalmitate (VCIP); nicotinic acid, its esters and nicotinamide (also called vitamin B3 or vitamin PP); nordihydroguaiaretic acid; urea; oligofucoses; cinnamic acid; derivatives of jasmonic acid; hydroxy stilbenes such as resveratrol; *Saccarum officinarum* extract; enzymes involved in desquamation or degradation of the corneodesmosomes, such as glycosidases, stratum corneum chymotryptic enzyme (SCCE) or other proteases such as trypsin, chymotrypsin, sutilain, papain or bromelain; chelating agents such as ethylenediaminetetraacetic acid (EDTA) and its salts, aminosulfonic compounds such as 4-(2-hydroxyethyl)piperazine-1-ethanesulfonic acid (HEPES) or sodium methylglycine diacetate (TRILON® M marketed by BASF); derivatives of 2-oxothiazolidine-4-carboxylic acid (procysteine); derivatives of sugars such as O-octanoyl-6-D-maltose and N-acetylglucosamine; chestnut extract (*Castanea sativa*) such as that marketed by SILAB under the trade name Recoverine® Water (Aqua), Castanea Sativa Seed Extract]; opuntia extract (Opuntia *ficus*-indica) such as that marketed by SILAB under the trade name Exfolactive® [INCI: Hydrolyzed Opuntia *Ficus* Indica Flower Extract]; or Phytosphingosine SLC® [INCI: Salicyloyl Phytosphingosine] marketed by Degussa/Evonik, Peel-Moist™ [INCI: Glycerin, Papain, Calcium Pantothenate, Xanthan Gum, Caprylyl Glycol, Urea, Magnesium Lactate, Ethylhexylglycerin, Potassium Lactate, Serine, Alanine, Proline, Magnesium Chloride, Sodium Citrate]; extract or combination of extracts of Saphora *japonica, papaya*, pineapple, pumpkin or sweet potato, and/or mixtures thereof.

In another particular embodiment, the anti-inflammatory agent and/or analgesic agent is selected, for example and not restricted to, from the group formed by madecassoside extract, *echinacea* extract, amaranth seed oil, sandal wood oil, peach tree leaf extract, extract of *Aloe vera, Arnica montana, Artemisia vulgaris, Asarum maximum, Calendula officinalis, Capsicum, Centipeda cunninghamii, Chamomilla recutita, Crinum asiaticum, Hamamelis virginiana, Harpagophytum procumbens, Hypericum perforatum, Lilium candidum, Malva sylvestris, Melaleuca altemifolia, Origanum majorana, Origanum vulgare, Prunus laurocerasus, Rosmarinus officialis, Salix alba, Silybum marianum, Tanacetum parthenium, Thymus vulgaris, Uncaria guianensis* or *Vaccinum myrtillus*, mometasone furoate, prednisolone, nonsteroidal antiinflammatories including cyclooxygenase or lipoxygenase inhibitors, benzydamine, acetylsalicylic acid, rosmarinic acid, ursolic acid, derivatives of glycyrrhizinate, α-bisabolol, azulene and analogues, sericoside, ruscogenin, escin, scoline, rutin and analogues, hydrocortisone, clobetasol, dexamethasone, prednisone, paracetamol, amoxiprin, benorilate, choline salicylate, faislamine, methyl salicylate, magnesium salicylate, salsalate, diclofenac, aceclofenac, acemetacin, bromfenac, etodolac, indomethacin, oxamethacin, proglumetacin, sulindac, tolmetin, ibuprofen, dexibuprofen, carprofen, fenbufen, fenoprofen, flurbiprofen, ketoprofen, dexketoprofen, ketorolac, loxoprofen, naproxen, miroprofen, oxaprozin, pranoprofen, tiaprofenic acid, suprofen, mefenamic acid, meclofenamate, meclofenamic acid, flufenamic acid, tolfenamic acid, nabumetone, phenylbutazone, azapropazone, clofezone, kebuzone, metamizole, mofebutazone, oxyphenbutazone, phenazone, sulfinpyrazone, piroxicam, lornoxicam, meloxicam, tenoxicam, celecoxib, etoricoxib, lumiracoxib, parecoxib, rofecoxib, valdecoxib, nimesulide, naproxcinod, fluproquazone or licofelone, omega-3 and omega-6 fatty acids, morphine, codeine, oxycodone, hydrocodone, diamorphine, pethidine, tramadol, bupenorphine, benzocaine, lidocaine, chloroprocaine, tetracaine, procaine, amitriptyline, carbamazepine, gabapentin, pregabalin, bisabolol, Neutrazen™ [INCI: Water, Butylene Glycol, Dextran, Palmitoyl Tripeptide-8] marketed by Atrium Innovations/Unipex Group, Meliprene® [INCI: Dextran, Acetyl Heptapeptide-1] marketed by Institut Europeen de Biologie Cellulaire/Unipex Group, Skinasensyl™ [INCI: Acetyl Tetrapeptide-15] or Anasensyl™ [INCI: Mannitol, Ammonium Glycyrrhizate, Caffeine, *Hippocastanum* (Horse Chestnut) Extract] marketed by Laboratoires Serobiologiques/Cognis, Calmosensine™ [INCI: Acetyl Dipeptide-1] marketed by Sederma, coenzyme Q10 or alkylglycerine ethers.

In addition, in another particular embodiment, the whitening or skin depigmenting agent is selected, for example and not restricted to, from the group formed by extracts of *Achillea millefolium, Aloe vera, Aradirachta indica, Asmuna japonica, Autocarpus incisus, Bidens pilosa, Broussonetia papyrifera, Chlorella vulgaris, Cimicifuga racemosa, Emblica officinalis, Glycyrrhiza glabra, Glycyrrhiza uralensis, Ilex purpurea, Ligusticum lucidum, Ligusticum wallichii, Mitracarpus scaber, Morinda citrifolia, Morus alba, Morus bombycis, Naringi crenulata, Prunus domesticus, Pseudostellariae radix, Rumex crispus, Rumex occidentalis, Sapindus mukurossi, Saxifragia sarmentosa, Scutellaria Galericulate, Sedum sarmentosum Bunge, Stellaria medica, Triticum Vulgare, Uva ursi* or *Whitania somnifera*, flavonoids, soy extract, lemon extract, orange extract, ginkgo extract, cucumber extract, geranium extract, gayuba extract, carob extract, cinnamon extract, marjoram extract, rosemary extract, clove extract, soluble liquorice extract or blackberry leaf extract, Lipochroman-6 [INCI: Dimethylmethoxy Chromanol] or Chromabright® [INCI: Dimethylmethoxy Chromanyl Palmitate] marketed by Lipotec, Actiwhite™ LS9808 [INCI: Aqua, Glycerin, Sucrose Dilaurate, Polysorbate 20, *Pisum sativum* (Pea) extract] or Dermawhite® NF LS9410 [INCI: Mannitol, Arginine HCl, Phenylalanine, Disodium EDTA, Sodium Citrate, Kojic Acid, Citric Acid, Yeast Extract] marketed by Laboratoires Serobiologiques/Cognis, Lumiskin™ [INCI: Caprylic/Capric Triglyceride, Diacetyl-Boldine], Melaclear™ [INCI: Glycerin, Aqua, Dithiaoctanediol, Gluconic acid, Sutilains, Beta-carotene], O.D.A.white™ [INCI: octadecendioic acid] or Etioline™ [INCI: Glycerin, Butylene Glycol, *Arctostaphylos uva ursi* Leaf Extract, *Mitracarpus scaber* Extract] marketed by Sederma, Sepiwhite™ MSH [INCI: Undecylenoyl Phenylalanine] marketed by Seppic, Achromaxyl™ [INCI: Aqua, *Brassica napus* Extract] marketed by Vincience, Gigawhite™ [INCI: Aqua, Glycerin, *Malva sylvestris* (Mallow) Extract, *Mentha piperita* Leaf Extract, *Primula veris* Extract, *Alchemilla vulgaris* Extract, *Veronica officinalis* Extract, *Melissa officinalis* Leaf Extract, *Achillea millefolium* Extract], Melawhite® [INCI: Leukocyte Extract, AHA] or Melfade®-J [INCI: Aqua, *Arctostaphylos uva-ursi* Leaf Extract, Glycerin, Magnesium Ascorbyl Phosphate] marketed by Pentapharm, Albatin® [INCI: Aminoethylphosphoric Acid, Butylene Glycol, Aqua] marketed by Exsymol, Tyrostat™-11 [INCI: Aqua, Glycerin, *Rumex occidentalis* Extract] or Melanostatine®-5 [INCI: Dextran, Nonapeptide-1] marketed by Atrium Innovations, arbutin and its isomers, kojic acid and derivatives thereof, ascorbic acid and derivatives thereof such as 6-O-palmitoylascorbic acid, ascorbyl glucoside, dipalmitoylascorbic acid, magnesium salt of ascorbic acid-2-phosphate (MAP), sodium salt of ascorbic acid-2-phosphate (NAP), ascorbyl glucoside or ascorbyl tetraisopalmitate (VCIP); retinol and derivatives thereof including tretinoin and isotretinoin, idebenone, hydroxybenzoic acid and derivatives thereof, niacinamide, liquiritin, resorcinol and derivatives thereof, hydroquinone, α-tocopherol, γ-tocopherol, azelaic acid, azeloyl diglycinate, resveratrol, linoleic acid, α-lipoic acid, dihydrolipoic acid, α-hydroxy acids, β-hydroxy acids, ellagic acid, ferulic acid, cinnamic acid, oleanolic acid, aloesin and its derivatives and/or serine protease inhibitors, for example and not restricted to, tryptase, trypsin or PAR-2 inhibitors, among others.

In another particular embodiment, the agent which stimulates the synthesis of melanin, the propigmenting agent, the self-tanning agent and/or the melanocyte proliferation stimulating agent is selected, for example and not restricted to, from the group formed by extracts of *Citrus Aurantium Dulcis* Fruit, *Coleus forskohlii, Coleus esquirolii, Coleus scutellariodes, Coleus xanthanthus, Ballota nigra, Ballota lanata, Ballota suavelens, Marrubium cylleneum, Cistus creticus, Amphiachyris amoena, Aster oharai, Otostegia fruticosa, Plectranthus barbatus, Halimium viscosum* or *Larix laricema*, dihydroxyacetone and derivatives thereof, sugars, for example and not restricted to, erythrulose, melanin and derivatives thereof including melanin polymers and derivatives of melanin with a low molecular weight which are soluble in water, forskolin and derivatives thereof including deacetylforskolin and isoforskolin, tyrosine and derivatives thereof including acetyl tyrosine, oleoyl tyrosine, 3-amino tyrosine and 3-nitrotyrosine, copper salts such as $CuCl_2$, carotenoids, canthaxanthins, polymers of dihydroxyindole carboxylic acid, 3,4-dihydroxybenzoic acid, 3-amino-4-hydroxybenzoic acid, aloin, emodin, alizarin, dihydroxyphenylalanine, 4,5-dihydroxynaphthalene-2-sulfonic acid, 3-dimethylaminophenol or p-aminobenzoic acid, Melatime™ [INCI: Acetyl Tripeptide-40] marketed by Lipotec, Heliostatine IS™ [INCI: *Pisum Sativum* Extract] marketed by Vincience/ISP, Vegetan® [INCI: Dihydroxyacetone] or Vegetan® Premium [INCI: Dihydroxyacetone, Melanin] marketed by Soliance, MelanoBronze™ [INCI: Vitex Agnus Castus Extract, Acetyl Tyrosine] marketed by Mibelle Biochemistry, Melitane® [INCI: Acetyl Hexapeptide-1] marketed by Institut Europeen de Biologie Cellulaire/Unipex Innovations, Actibronze® [INCI: Hydrolyzed Wheat Protein, Acetyl Tyrosine, Copper Gluconate] or Instabronze® [INCI: Dihydroxyacetone, Tyrosine] marketed by Alban Muller, Thalitan® [INCI: Hydrolyzed Algin, Magnesium Sulfate, Manganese Sulfate] marketed by CODIF, Tyrosilane® [INCI: Methylsilanol Acetyltyrosine] marketed by Exsymol, Tyr-Excel™ [INCI: Oleoyl Tyrosine, Luffa *Cylindrica* Seed Oil, Oleic Acid] or Tyr-Ol™ [INCI: Oleoyl Tyrosine, Butylene glycol, Oleic Acid] marketed by Sederma/Croda, Bronzing S.F.™ [proposed INCI: Butiryl Pentapeptide] marketed by Infinitec Activos or Biotanning® [INCI: Hydrolyzed Citrus *Aurantium dulcis* Fruit Extract] marketed by Silab, among others.

In a particular embodiment, the anti-wrinkle and/or anti-aging agent is selected, for example and not restricted to, from the group formed by extracts of *Vitis vinifera, Rosa canina, Curcuma longa, Iris paffida, Theobroma cacao, Ginkgo biloba, Leontopodium alpinum* or *Dunaliella salina*, Matrixyl® [INCI: Palmitoyl Pentapeptide-4], Matrixyl 3000® [INCI: Palmitoyl Tetrapeptide-7, Palmitoyl Oligopeptide], Essenskin™ [INCI: calcium hydroxymethionine], Renovage™ [INCI: teprenone] or Dermaxyl® [INCI: Palmitoyl Oligopeptide] marketed by Sederma, Vialox® [INCI: Pentapeptide-3], Syn®-Ake® [INCI: Dipeptide Diaminobutyroyl Benzylamide Diacetate], Syn®-Coll [INCI: Palmitoyl Tripeptide-5], Phytaluronate® [INCI: Locust Bean (*Ceratonia Siliqua*) Gum] or Preregen® [INCI: *Glycine Soja* (Soybean) Protein, Oxido Reductases] marketed by Pentapharm/DSM, Myoxinol™ [INCI: Hydrolyzed Hibiscus *Esculentus* Extract], Syniorage™ [INCI: Acetyl Tetrapeptide-11], Dermican™ [INCI: Acetyl Tetrapeptide-9] or DN-AGE™ LS [INCI: *Cassia Alata* leaf Extract] marketed by Laboratoires Serobiologiques/Cognis, Algisum [INCI: Methylsilanol Mannuronate] or Hydroxyprolisilane CN® [INCI: Methylsilanol Hydroxyproline Aspartate] marketed by Exsymol, Argireline® [INCI: Acetyl Hexapeptide-8], SNAP-7 [INCI: Acetyl Heptapeptide-4], SNAP-8 [INCI: Acetyl Octapeptide-3], Leuphasyl® [INCI: Pentapeptide-18], Aldenine® [INCI: Hydrolyzed wheat protein, hydrolyzed soy protein, Tripeptide-1], Preventhelia® [INCI: Diaminopropionoyl Tripeptide-33], Decorinyl™ [INCI: Tripeptide-10 Citrulline], Trylagen® [INCI: *Pseudoalteromonas* Ferment Extract, Hydrolyzed Wheat Protein, Hydrolyzed Soy Protein, Tripeptide-10 Citrulline, Tripeptide-1], Eyeseryl® [INCI: Acetyl Tetrapeptide-5], Peptide AC29 [INCI: Acetyl Tripeptide-30 Citrulline], Lipochroman™-6 [INCI: Dimethylmethoxy Chromanol], Chromabright™ [INCI: Dimethylmethoxy Chromanyl Palmitate], Antarcticine® [INCI: *Pseudoalteromonas* Ferment Extract], Vilastene™ [INCI: Lysine HCl, Lecithin, Tripeptide-10 Citrulline], dGlyage™ [INCI: Lysine HCl, Lecithin, Tripeptide-9 Citrulline], Relistase™ [INCI: Acetylarginyltriptophyl Diphenylglycine] or Inyline™ [INCI: Acetyl Hexapeptide-30] marketed by Lipotec, Kollaren® [INCI: Tripeptide-1, Dextran] marketed by Institut Europeen de Biologie Cellulaire, Collaxyl® IS [INCI: Hexapeptide-9], Laminixyl IS™ [INCI: Heptapeptide], Orsirtine™ GL [INCI: *Oryza Sativa* (Rice) Extract], D'Orientine™ IS [INCI: *Phoenix Dactylifera* (Date) Seed Extract], Phytoquintescine™ [INCI: Einkorn (*Triticum Monococcum*) Extract] or Quintescine™ IS [INCI: Dipeptide-4] marketed by Vincience/ISP, BONT-L-Peptide™ [INCI: Palmitoyl Hexapeptide-19] marketed by Infinitec Activos, Deepaline™ PVB [INCI: Palmitoyl hydrolyzed Wheat Protein] or Sepilift® DPHP [INCI: Dipalmitoyl Hydroxyproline] marketed by Seppic, Gatuline® Expression [INCI: *Acmella oleracea* Extract], Gatuline® In-Tense [INCI: Spilanthes *Acmella* Flower Extract] or Gatuline® Age Defense 2 [INCI: *Juglans Regia* (Walnut)

Seed Extract] marketed by Gattefossé, Thalassine™ [INCI: Algae Extract] marketed by Biotechmarine, ChroNOline™ [INCI: Caprooyl Tetrapeptide-3] or Thymulen®-4 [INCI: Acetyl Tetrapeptide-2] marketed by Atrium Innovations/Unipex Group, EquiStat™ [INCI: *Pyrus* Malus Fruit Extract, *Glycine Soja* Seed Extract] or Juvenesce™ [INCI: Ethoxydiglicol and Caprylic Triglyceride, Retinol, Ursolic Acid, Phytonadione, Ilomastat] marketed by Coletica, Ameliox™ [INCI: Carnosine, Tocopherol, *Silybum Marianum* Fruit Extract] or PhytoCellTec™ *Malus Domestica* [INCI: *Malus Domestica* Fruit Cell Culture] marketed by Mibelle Biochemistry, Bioxilift™ [INCI: Pimpinella Anisum Extract] or SMS Anti-Wrinkle® [INCI: Annona *Squamosa* Seed Extract] marketed by Silab, $Ca^{2+}$ channel blockers, for example and not restricted to, alverin, manganese or magnesium salts, certain secondary or tertiary amines, retinol and derivatives thereof, resveratrol, idebenone, coenzyme Q10 and derivatives thereof, boswellic acid and derivatives thereof, GHK and derivatives thereof and/or salts, carnosine and derivatives thereof, DNA repair enzymes, for example and not restricted to, photolyase or T4 endonuclease V, or chloride channel blockers among others.

In a particular embodiment, the lipolytic agent or agent stimulating lipolysis, venotonic agent and/or anti-cellulite agent is selected, for example and not restricted to, from the group formed by extracts of *Bupleurum Chinensis, Cecropia Obtusifolia, Celosia Cristata, Centella Asiatica, Chenopodium Quinoa, Chrysanthellum Indicum, Citrus Aurantium Amara, Coffea Arabica, Coleus Forskohlii, Commiphora Myrrha, Crithmum Maritimum, Eugenia Caryophyllus, Ginkgo Biloba, Hedera Helix* (ivy extract), *Hibiscus Sabdariffa, Ilex Paraguariensis, Laminaria Digitata, Nelumbium Speciosum, Paullinia Cupana, Peumus Boldus, Phyllacantha Fibrosa, Prunella Vulgaris, Prunus Amygdalus Dulcis, Ruscus Aculeatus* (Butcherbroom extract), *Sambucus Nigra, Spirulina Platensis* Algae, *Uncaria Tomentosa* or *Verbena Officinalis*, dihydromyricetin, coenzyme A, lipase, glaucine, esculin, visnadine, Regu®-Shape [INCI: Isomerized Linoleic Acid, Lecithin, Glycerin, Polysorbate 80] marketed by Pentapharm/DSM, UCPeptide™ V [INCI: Pentapeptide] or AT Peptide™ IS [INCI: Tripeptide-3] marketed by Vincience/ISP, Liporeductyl® [INCI: Caffeine, Butcherbroom (*Ruscus Aculeatus*) Root Extract, TEA-Hydroiodide, Carnitine, Ivy (*Hedera Helix*) Extract, Escin, Tripeptide-1] marketed by Lipotec, Adiposlim™ [INCI: Sorbitan Laurate, Lauroyl Proline] marketed by SEPPIC, caffeine, carnitine, escin and/or triethanolamine iodide, among others.

In a particular embodiment, the heat shock protein synthesis stimulating agent is selected, for example and not restricted to, from the group formed by extracts of *Opuntia ficus* indica, *Salix alba, Lupinus* spp., *Secale cereale*, extracts of red algae from the genus *Porphyra*, extracts of crustaceans from the genus *Artemia*, jojoba seed oil, grape seed extracts, green tea extracts, geranylgeranylacetone, celastrol, zinc and its salts, 2-cyclopenten-1-one, proteasome inhibitors, for example and not restricted to, bortezomib; prostaglandins and derivatives thereof, hydroxylamine and derivatives thereof, for example and not restricted to, bimoclomol; chalcone and derivatives thereof, hyperosmotic agents, for example and not restricted to, sorbitol and derivatives thereof, mannitol and derivatives thereof or glycerol and derivatives thereof, isosorbide, urea or salicylic acid and derivatives thereof among others, Thermostressine™ [INCI: Acetyl Tetrapeptide-22], or mixtures thereof.

In another particular embodiment, the hair growth inducing agent, the agent which acts on capillary circulation and/or microcirculation, or the hair loss retardant agent is selected, for example and not restricted to, from the group formed by the extracts of *Tussilago farfara* or *Achillea millefolium*, nicotinic acid esters such as $C_3$-$C_6$ alkyl nicotinates such as methyl or hexyl nicotinate, benzyl nicotinate, or tocopheryl nicotinate; biotin, 5α-reductase-inhibiting agents, anti-inflammatory agents, retinoids, for example and not restricted to, all-trans-retinoic acid or tretinoin, isotretinoin, retinol or vitamin A, and derivatives thereof, such as zinc salt of acetate, palmitate, propionate, motretinide, etretinate and trans-retinoate; anti-bacterial agents, calcium channel blockers, for example and not restricted to, cinnarizine and diltiazem; hormones, for example and not restricted to, estriol, its analogues or thyroxine, its analogues and/or salts; antiandrogenic agents, for example and not restricted to, oxendolone, spironolactone or diethylstilbestrol; antiradical agents, esterified oligosaccharides, for example and not restricted to, those described in documents EP 0211610 and EP 0064012; derivatives of hexosaccharic acids, for example and not restricted to, glucosaccharic acid or those described in document EP 0375388; glucosidase inhibitors, for example and not restricted to, D-glucaro-1,5-lactam or those described in document EP 0334586; glycosaminoglycanase and proteoglycanase inhibitors, for example and not restricted to L-galactono-1,4-lactone or those described in document EP 0277428; tyrosine kinase inhibitors, for example and not restricted to, 1-amido-1-cyano(3,4-dihydroxyphenyl)ethylene or those described in document EP 0403238, diazoxides, for example and not restricted to, 7-(acetylthio)-4',5'-dihydrospiro[androst-4-ene-17,2'-(3H) furan]-3-one, 1,1-dioxide of 3-methyl-7-chloro[2H]-1,2,4-benzothiadiazine or spirooxazine; phospholipids, for example and not restricted to, lecithin; salicylic acid and derivatives thereof, hydroxycarboxylic or keto carboxylic acids and esters thereof, lactones and their salts; anthralin, eicosa-5,8,11-trienoic acids and esters thereof or amides among others, minoxidil and derivatives or mixtures thereof.

In another particular embodiment the body hair growth inhibiting or retardant agent is selected, for example and not restricted to, from the group formed by activin or activin agonists, flavonoids such as quercetin, curcumin, galangin, fisetin, myricetin, apigenin; propyl gallate, nordihydroguaiaretic acid, caffeic acid, tyrosine kinase inhibitors such as lavendustin, erbstatin, tyrphostins, benzoquinone-ansamycin herbimycin A, thiazolidinediones, phenazocine, 2,3-dihydro-2-thioxo-1H-indol-3-alcanoic acids, phenothiazine derivatives such as thioridazine; sphingosine and derivatives thereof, staurosporine and derivatives thereof, glycyrrhetinic acid, lauryl isoquinolinium bromide, Decelerine™ [INCI: Lauryl Isoquinolium Bromide, *Pseudoalteromonas* Ferment Extract] marketed by Lipotec or serine protease inhibitors, trypsin and/or mixtures thereof.

In a particular embodiment, the cosmetic and/or absorbent and/or body odor masking deodorant and/or antiperspirant agent, perfuming substance and/or perfumed oil is selected, for example and not restricted to, from the group formed by the complex zinc salt of ricinoleic acid, *Styrax*, derivatives of abiotic acid, sage essence, chamomile essence, carnation essence, lemon balm essence, mint essence, cinnamon leaf essence, lime flower essence, juniper berry essence, vetiver essence, olibanum essence, *galbanum* essence, labdanum essence, lavender essence, peppermint essence, bergamot orange, dihydromyrcenol, lilial, lyral, citronellol, lemon essence, mandarin essence, orange essence, lavender essence, muscat, geranium bourbon essence, aniseed, cilantro, cumin, juniper, extracts of fleur-de-lis, lilac, roses, jasmin, bitter orange blossom; benzyl acetate, p-tert-butylcyclohexyl acetate, linalyl acetate, phenylethyl acetate, ethylmethylphenyl glycinate, linalyl benzoate, benzyl formate, allyl cyclohexyl propionate, styrallyl propionate, benzyl salicylate, benzyl ethyl ether, linear alkanes with from 8 to 18 carbon atoms, citral, ricinoleic acid, citronellal, citronellyl oxyacetaldehyde, cyclamen aldehyde, hydroxycitronellal, bourgeonal, ionones, methyl cedryl ketone, anethole, eugenol, isoeugenol, geraniol, linalool, terpineol, phenylethyl alcohol, α-hexylcinnamaldehyde, geraniol, benzylacetone, cyclamen aldehyde, ambroxan, indole, hedione, sandelice, cyclovertal, β-damascone, allyl amyl glycolate, dihydromyrcenol, phenoxyethyl isobutyrate, cyclohexyl salicylate, phenylacetic acid, geranyl acetate, romillat, irotyl, floramate, active astringent products such as aluminum chloride, aluminum chlorohydrate, aluminum dichlorohydrate, aluminum sesquichlorohydrate, aluminum hydroxyallantoinate, aluminum chlorotartrate, aluminum and zirconium trichlorohydrate, aluminum and zirconium tetrachlorohydrate, aluminum and zirconium pentachlorohydrate and/or mixtures thereof.

In a particular embodiment, the antioxidant is selected, for example and not restricted to, from the group formed by butylhydroxytoluene (BHT), butylhydroxyanisole (BHA), tert-butylhydroquinone (TBHQ), 2,6-di-tert-butyl-4-methylphenol, gallic acid esters such as propyl gallate, probucol, polyphenoles, ascorbic acid and its salts, enzymes such as catalase, superoxide dismutase and peroxidases; citric acid, citrates, monoglyceride esters, calcium metabisulfate, lactic acid, malic acid, succinic acid, tartaric acid, vitamin A or β-carotene, vitamins E and C, tocopherols such as vitamin E acetate, ascorbic acid esters such as ascorbyl palmitate and ascorbyl acetate, zinc, copper, mannitol, reduced glutathione, carotenoids such as cryptoxanthin, astaxanthin and lycopene; cysteine, uric acid, carnitine, taurine, tyrosine, lutein, zeaxanthin, N-acetyl-cysteine, carnosine, γ-glutamylcysteine, quercetin, lactoferrin, dihydrolipoic acid, tea catechins, retinyl palmitate and derivatives thereof, bisulfate, metabisulfite and sodium sulfite, chromans, chromens and their analogues, Lipochroman™-6 [INCI: Dimethylmethoxy Chromanol], chelating agents of metals such as EDTA, sorbitol, phosphoric acid or dGlyage™ [INCI: Lysine HCl, Lecithin, Tripeptide-9 Citrulline]; extract of Ginkgo Biloba, plant extracts such as sage, pomegranate, rosemary, oregano, ginger, marjoram, cranberry, grape, tomato, green tea or black tea; oleoresin extract, extract of plants which contain phenols such as vanillin, ellagic acid and resveratrol; tertiary butylhydroquinone or mixtures thereof, metal salts with a valence of 2 such as selenium, cadmium, vanadium or zinc; α-lipoic acid, coenzyme Q, idebenone or derivatives thereof.

In a particular embodiment, the agent inhibiting sweat-degrading enzymes is selected, for example and not restricted to, from the group formed by trialkyl citrates such as trimethyl citrate, tripropyl citrate, triisopropyl citrate, tributyl citrate or triethyl citrate; lanosterine sulfate or phosphate, cholesterin, campesterin, stigmasterin and sitosterin; dicarboxylic acids and their esters, such as glutaric acid, monoethyl glutarate, diethyl glutarate, adipic acid, monoethyl adipate, diethyl adipate; malonic acid and diethyl malonate, hydroxycarboxylic acids and their esters such as malic acid, tartaric acid or diethyl tartrate, zinc glycinate and/or mixtures thereof.

In another particular embodiment, the agent capable of filtering UV rays is selected, for example and not restricted to, from the group formed by organic or mineral photoprotective agents active against A and/or B ultraviolet rays such as substituted benzotriazoles, substituted diphenylacrylates, organic nickel complexes, umbelliferone, urocanic acid, biphenyl derivatives, stilbene, 3-benzylidene camphor, and derivatives thereof such as 3-(4-methylbenzylidene)camphor; derivatives of 4-aminobenzoic acid, 2-ethylhexyl 4-(dimethylamino)benzoate, 2-octyl 4-(dimethylamino)benzoate and amyl 4-(dimethylamino)benzoate; cinnamic acid esters, such as 2-ethylhexyl 4-methoxycinnamate or diethylamino hydroxybenzoyl hexyl benzoate, propyl 4-methoxycinnamate, isoamyl 4-methoxycinnamate, 2-ethylhexyl (octocrylenes) 2-cyano-3,3-phenyl cinnamate; salicylic acid esters, such as 2-ethylhexyl salicylate, 4-isopropylbenzyl salicylate, homomenthyl salicylate; benzophenone derivatives, such as 2-hydroxy-4-m ethoxybenzophenone, 2-hydroxy-4-methoxy-4'-methylbenzophenone, 2,2'-dihydroxy-4-methoxybenzophenone; benzalmalonic acid esters, such as di-2-ethylhexyl 4-methoxybenzalmalonate; triazine derivatives, such as 2,4,6-trianilino, p-carbo-2'-ethyl-1'-hexyloxy-1,3,5-triazine, octyl triazone or dioctyl butamido triazones; propane-1,3-diones, such as 1-(4-tert-butylphenyl)-3-(4'-methoxyphenyl) propane-1,3-dione; ketotricyclo(5.2.1.0)decane derivatives; 2-phenylbenzimidazole-5-sulfonic acid; benzophenone sulfonic acid derivatives, such as 2-hydroxy-4-methoxybenzophenone-5-sulfonic acid and its salts; 4-(2-oxo-3-bornylidenemethyl)benzenesulfonic acid, benzoyl methane derivatives, such as benzoyl methane 2-methyl-5-(2-oxo-3-bornylidene)sulfonic acid, such as 1-(4'-tert-butylphenyl)-3-(4'-methoxyphenyl)propane-1,3-dione, 4-tert-butyl-4'-methoxydibenzoylmethane, 1-phenyl-3-(4'-isopropylphenyl)-propane-1,3-dione, enamine compounds, anthranilates, silicons, benzimidazole derivatives, imidazolines, benzoyl derivatives, Chromabright™ [INCI: Dimethylmethoxy Chromanyl Palmitate] or Preventhelia® [INCI: Diaminopropionoyl Tripeptide-33] both marketed by Lipotec, metal oxides such as zinc oxide, titanium, iron, zirconium, silicon, manganese, aluminum and cerium; silicates, talc, barium sulfate, zinc stearate, carbon nanotubes and/or mixtures thereof.

In addition, in another particular embodiment, the agent stimulating or regulating keratinocyte differentiation is selected, for example and not restricted to, from the group formed by minerals such as calcium, retinoids such as retinol or tretinoin, analogues of vitamin D3 such as calcitriol, calcipotriol or tacalcitol, lupine (Lupinus albus) extract such as that marketed by SILAB under the trade name Structurin® [INCI: Hydrolyzed Lupine Protein], β-sitosterol sulfate, such as that marketed by Vincience/ISP under the trade name Phytocohesine PSP® [INCI: Sodium Beta-sitosterol Sulfate], maize (Zea Mays) extract such as that marketed by Solabia under the trade name Phytovityl C® [INCI: Water (Aqua), Zea Mays Extract], Helix Aspersa Müller glycoconjugates and/or mixtures thereof.

Likewise, in another particular embodiment, the muscle relaxant, agent inhibiting muscle contraction, agent inhibiting acetylcholine receptor clustering and/or anticholinergic agent is selected, for example and not restricted to, from the group formed by extracts of Atropa belladonna, Hyoscyamus niger, Mandragora officinarum, Chondodendron tomentosum, plants of the Brugmansia genus, or the Datura genus, Clostridium botulinum toxin, peptides derived from the protein SNAP-25 or Inyline™ [INCI: Acetyl Hexapeptide-30] marketed by Lipotec, baclofen, carbidopa, levodopa, bromocriptine, chlorphenesin, chlorzoxazone, donepezil, mephenoxalone, reserpine, tetrabenazine, dantrolene, thiocolchicoside, tizanidine, clonidine, procyclidine, glycopyrrolate, atropine, hyoscyamine, benztropine, scopolamine, promethazine, diphenhydramine, dimenhydrinate, dicyclomine, cyclobenzaprine, orphenadrine, flavoxate, cyclopentolate, ipratropium, oxybutynin, pirenzepine, tiotropium, trihexyphenidyl, tolterodine, tropicamide, solifenacin, darifenacin, mebeverine, trimethaphan, atracurium, cisatracurium, doxacurium, fazadinium, metocurine, mivacurium, pancuronium, pipecuronium, rapacuronium, tubocuranine, dimethyl tubocuranine, rocuronium, vecuronium, suxamethonium, 18-methoxycoronaridine, carisoprodol, febarbamate, meprobamate, metocarbamol, phenprobamate, tibamate, anticonvulsant agents such as levetiracetam, stiripentol, phenobarbital, methylphenobarbital, pentobarbital, metharbital, barbexaclone, pirimidone, carbamazepine, oxcarbazepine, benzodiazepines, for example and not restricted to, clonazepam, cloxazolam, clorazepate, diazepam, flutoprazepam, lorazepam, midazolam, nitrazepam, nimetazepam, phenazepam, temazepam, tetrazepam or clobazam, among others.

In another particular embodiment, the nanocapsules of this invention comprise other pharmaceutical active ingredients and/or adjuvants of any nature, hydrophobes, hydrophiles or amphiphiles, which can be found inside the nanocapsules in solution or in suspension in the lipid matrix, or in the aqueous phase of the microemulsion. In particular, the pharmaceutical active ingredients and/or adjuvants are selected, for example and not restricted to, from the group formed by antiacids, agents against peptic ulcers and gastroesophageal reflux disease, antispasmodics, analgesics, anticholinergic drugs, propulsive drugs, antiemetics, antinausea drugs, agents for biliary therapy, agents for hepatic therapy, lipotropics, laxatives, antidiarrhetics, intestinal adsorbents, antipropulsives, anti-inflammatory drugs, active ingredients against obesity, enzymes, hypoglycemic drugs, insulin and analogues, vitamins, proteins, minerals, anabolic steroids, antithrombotic agents, antifibrinolytics, haemostatic agents, antiarrhythmic agents, cardiac stimulants, cardiac glycosides, vasodilators, antiadrenergic agents, antihypertensive drugs, diuretics, potassium-saving agents, antihemorrhoidals, antivaricose therapy agents, capillary stabilizing agents, agents which act on the renin-angiotensin system, beta-blockers, selective calcium-channel blockers, non-selective calcium-channel blockers, ACE inhibitors, angiotensin II inhibitors, agents modifying lipids, antifungals, healing agents, antipruritics, antihistamines, anesthetics, antipsoriatics, chemotherapy drugs, corticosteroids, antiseptics, disinfectants, anti-acne agents, products for gynecological use, oxytocics, anticonceptives, androgen, estrogen, progestagen, ovulation stimulants, gonadotropins, antiandrogens, products for urological use, antispasmodics, drugs used in benign prostatic hypertrophy, hormones, hormone antagonists, antibiotics, tetracyclines, anphenicols, beta-lactam antibacterials, penicillin, sulfonamides, trimethoprim, macrolides, lincosamides, streptogram ins, antibacterial am inoglycosides, antibacterial quinolones, antivirals, immune serum, immunoglobulins, antineoplastic agents, immunomodulatory agents, alkylation agents, antimetabolites, plant alkaloids and other natural products, cytotoxic antibiotics, immunosuppressive agents, drugs for disorders of the musculoskeletal system, antirheumatics, muscle relaxant agents, agents which affect bone structure and mineralization, drugs which act on the nervous system, general anesthetics, local anesthetics, opioids, antimigraine agents, anticonvulsants, anticholinergic agents, dopaminergic agents, antipsychotics, anxiolytics, hypnotics, sedatives, antidepressants, psychostimulants, anti-dementia drugs, parasympathomimetics, drugs used in addictive disorders, anti-vertigo agents, antiparasitic agents, insecticides, insect repellants, nasal decongestants, mucolytic agents, cough suppressants, ophthalmic active ingredients, otological active ingredients, antiglaucoma drugs, miotics, mydriatics, cycloplegics and/or mixtures thereof.

In another particular embodiment, the nanocapsules of this invention which contain cosmetic and/or pharmaceutical active ingredients and/or adjuvants can be incorporated into to natural or synthetic fibers of textile materials before or after their manufacture. In this invention textile materials are understood to be woven fabrics, non-woven fabrics, garments and medical devices. These textile materials, in direct contact with the body's skin, release the active ingredients incorporated into the delivery system of this invention either by biodegradation of the of the binding system to the woven fabric, non-woven fabric or medical device or due to friction between these and the body, due to body moisture, the pH of the skin or body temperature. Examples of woven fabrics, non-woven fabrics, garments, medical devices and means for immobilization of delivery systems can be found in the prior art (*J. Cont. Release* 2004, 97, 313-320). Means for immobilization of delivery systems in preferred textile materials are the application by means of a foulard, exhaustion bath or spraying. The natural and/or synthetic fibers can be wool, cotton, silk, nylon fibers, cellulose, polyamide or polyester among others. Among the textile materials the preferred woven fabrics, non-woven fabrics, garments and medical devices are bandages, gauzes, t-shirts, socks, tights, underwear, girdles, gloves, diapers, sanitary napkins, dressings, bedspreads, wipes, hydrogels, adhesive patches, non-adhesive patches, micro-electric patches and/or face masks.

According to another aspect, this invention relates to a cosmetic, pharmaceutical and/or alimentary composition which comprises the nanocapsules of this invention.

The nanocapsules of this invention can also be adsorbed onto solid organic polymers or solid mineral supports, for example and not restricted to talc, bentonite, silica, starch or maltodextrin among others.

The nanocapsules of this invention can be incorporated into any form of functional food or enriched food, or into oral cosmetics or nutricosmetics, and formulated with the usual excipients and adjuvants for oral compositions or alimentary supplements, for example and not restricted to, fatty components, aqueous components, humectants, preservatives, texturizing agents, flavors, aromas, antioxidants and food coloring commonly used in food industry.

The cosmetic, pharmaceutical and/or alimentary compositions which comprise the nanocapsules of this invention can be prepared by the conventional methods known by the people skilled in the art. The cosmetic, pharmaceutical and/or alimentary compositions which incorporate the nanocapsules of this invention can be a final composition, available for application without having to carry out any kind of concentration, solution, dilution, dispersion, pulverization, spraying procedure or any other similar procedure known by the person skilled in the art, or an intermediate composition to which one or several of the previous procedures will be carried out or any other procedure known by the person skilled in the art with the aim of obtaining a final composition.

The cosmetic, pharmaceutical and/or alimentary compositions which comprise the nanocapsules of this invention can be administered by topical or transdermal administration, orally, or by any other type of suitable route, for example parenteral, and the cosmetically and/or pharmaceutically acceptable excipients necessary for the formulation of the desired method of administration will be included. In the context of this invention, the term "parenteral" includes nasal, auricular, ophthalmic, rectal, urethral and vaginal routes, subcutaneous, intradermal, intravascular, such as intravenous, intramuscular, intraocular, intravitreal, intracorneal, intraspinal, intramedullary, intracranial, intracervical, intracerebral, intrameningeal, intraarticular, intrahepatic, intrathoracic, intratracheal, intrathecal and intraperitoneal injections, as well as any another similar injection or infusion technique.

The cosmetic and/or pharmaceutical compositions which comprise the nanocapsules of this invention can be used in different types of compositions of topical and transdermal application which optionally will include the cosmetically and/or pharmaceutically acceptable excipients necessary for the formulation of the desired method of administration. The compositions of topical or transdermal application may be presented in any solid, liquid or semi-solid formulation, for example and not restricted to, creams, multiple emulsions, for example and not restricted to, oil and/or silicone in water emulsions, water-in-oil and/or silicone emulsions, water/oil/water or water/silicone/water type emulsions, and oil/water/oil or silicone/water/silicone type emulsions, anhydrous compositions, aqueous dispersions, oils, milks, balsams, foams, lotions, gels, cream gels, hydroalcoholic solutions, hydroglycolic solutions, hydrogels, liniments, sera, soaps, shampoos, conditioners, serums, polysaccharide films, ointments, mousses, pomades, powders, bars, pencils and sprays or aerosols, including leave-on and rinse-off formulations. These formulations of topical and transdermal application can be incorporated by techniques known by the people skilled in the art into different types of solid accessories, for example and not restricted to, bandages, gauzes, t-shirts, socks, tights, underwear, girdles, gloves, diapers, sanitary napkins, dressings, bedspreads, wipes, adhesive patches, non-adhesive patches, microelectric patches or face masks, or can be incorporated into different make-up products such as make-up foundation, for example fluid foundations and compact foundations, make-up removal lotions, make-up removal milks, under-eye concealers, eye shadows, lipsticks, lip protectors, lip gloss and powders, among others. The cosmetic or dermopharmaceutical compositions of this invention can also be incorporated into products for the treatment and/or care of nails and cuticles such as nail varnishes, nail varnish remover lotions and cuticle remover lotions, among others.

The cosmetic, pharmaceutical and/or alimentary compositions which comprise the nanocapsules of this invention can be used in different types of formulations for oral administration, preferably in the form of oral cosmetics or drugs, for example and not restricted to, capsules, including gelatin capsules, soft capsules, hard capsules, tablets, including sugar coated tablets, powders, granules, chewing gum, solutions, suspensions, emulsions, syrups, polysaccharide films, jellies or gelatins, and any other form known by the person skilled in the art.

In another particular embodiment, the compositions which comprise the nanocapsules of this invention can be used for the treatment of textile materials and can be found in washing agents in liquid form, as well as detergents, in the manufacturing of emulsions, rinse aids, rinsing agents, fabric softener, sprays, liquid soaps or gels, or also in solid form, such as powder, granules or compact products. In addition, these compositions contain other components, for example and not restricted to, surfactants, agents which increase percutaneous absorption, agents for the prior treatment of textile materials, agents for the treatment of marks, abrasives, water softeners, fabric softeners, solvents or solubilizing agents, agents for the variation of touch and finish, dirt-repelling agents, antistatic agents, enzymes, agents which aid ironing, color and/or colorant brightening agents, shine agents, optical clearing agents, graying inhibitors or compounds for the loosening of dirt, color transfer inhibitors, phobizing and impregnating agents, swelling or thickening agents, consistency-generating agents, silicon agents, agents which increase the percutaneous absorption of microcapsules, whitening agents and textile material bleaching activators, hydrophilization agents and/or mixtures thereof.

Another aspect of this invention relates to the use of cosmetic, pharmaceutical and/or alimentary compositions which comprise the nanocapsules of this invention for the treatment and/or care of the skin, scalp, hair and nails. Preferably the treatment and/or care of the skin, hair, scalp and/or nails is selected from the group formed by treatment and/or prevention of skin aging, healing of the skin and/or scalp, dermatological treatment of skin diseases, treatment and/or prevention of cellulitis, skin tanning, skin lightening or whitening and treatment and/or prevention of hair loss.

In the context of this invention, the term "aging" relates to the changes experienced by the skin with age (chronoaging) or due to exposure to the sun (photoaging) or to environmental agents such as tobacco smoke, extreme climatic conditions of cold or wind, chemical pollutants or pollution, and includes all the external visible changes as well as those noticeable by touch, for example and not restricted to, the development of discontinuities on the skin such as wrinkles, fine lines, furrows, irregularities or roughness, increase in the size of pores, loss of elasticity, loss of firmness, loss of smoothness, loss of the capacity to recover from the deformation, sagging of the skin such as sagging cheeks, the appearance of bags under the eyes or the appearance of a double chin among others, changes to the color of the skin such as marks, reddening, bags under the eyes, appearance of hyperpigmented areas such as age spots or freckles among others, anomalous differentiation, hyperkeratinization, elastosis, keratosis, hair loss, orange-peel skin, loss of collagen structure and other histological changes of the stratum corneum, of the dermis, epidermis, vascular system (for example the appearance of spider veins or telangiectasias) or of tissues close to the skin, among others.

Another aspect of this invention relates to the use of cosmetic, pharmaceutical and/or alimentary compositions which contain the nanocapsules of this invention for the treatment of textile materials.

The following specific examples provided herein serve to illustrate the nature of this invention. These examples are included solely for illustrative purposes and should not be construed as limitations on the invention claimed herein.

EXAMPLES

In the following: Ala=Alanine, Arg=Arginine, Asn=Asparagine, Cit=Citrulline, Dpr=2,3-Diaminopropionic acid, Gln=Glutamine, Glu=Glutamic acid, His=Histidine, and Met=Methionine.
General Methodology All the reagents and solvents are of synthesis quality and are used without any additional treatment.

The high-pressure homogenizations were carried out in a "M110-Y"™ model microfluidizer by Microfluidics. The Ultraturrax® mixer for the formation of microemulsions is the "D-8" model by Miccra RT.

Hydrophilic thermolabile peptides in the form of microemulsion were nanoencapsulated by means of complex coacervation. The lipid matrix of the nanocapsules contained just liquid lipids or oils, thus it was not necessary to apply heat throughout the whole process and the degradation of the peptides was avoided.

Prophetic Example 1

Prophetic preparation of microemulsions of hydrophilic peptides for their subsequent encapsulation in coacervate nanocapsules which contain liquid lipids.

Example 1-a. Microemulsion of the Peptide H-Dpr-Ala-Asn-his-OH

Ducosate [INCI: DIETHYLHEXYL SODIUM SULFO-SUCCINATE] and isostearic acid [INCI: ISOSTEARIC ACID] (phase A) are mixed together in a suitable vessel.

In another vessel the peptide H-Dpr-Ala-Asn-His-OH is dissolved in ethanol [INCI: ALCOHOL]. Once dissolved, water is added (phase B).

Phase B is added to Phase A slowly under stirring.

| | INGREDIENT (INCI Nomenclature) | % IN WEIGHT |
|---|---|---|
| A | DIETHYLHEXYL SODIUM SULFOSUCCINATE/ISOSTEARIC ACID (15/85) | 89.75 |
| B | H-Dpr-Ala-Asn-His-OH | 0.25 |
| B | WATER (AQUA) | 7.00 |
| B | ALCOHOL | 3.00 |

Example 1-b. Microemulsion of the Peptide Ac-Arg-Asn-his-Cit-NH$_2$

Ducosate [INCI: DIETHYLHEXYL SODIUM SULFO-SUCCINATE] and isostearic acid [INCI: ISOSTEARIC ACID] (phase A) are mixed together in a suitable vessel.

In another vessel the peptide Ac-Arg-Asn-His-Cit-NH$_2$ is dissolved in water. Once dissolved, ethanol [INCI: ALCOHOL] (phase B) is added.

Phase B is added to Phase A slowly under stirring.

| | INGREDIENT (INCI Nomenclature) | % IN WEIGHT |
|---|---|---|
| A | DIETHYLHEXYL SODIUM SULFOSUCCINATE/ISOSTEARIC ACID (15/85) | 89.84 |
| B | Ac-Arg-Asn-His-Cit-NH$_2$ | 0.16 |
| B | WATER (AQUA) | 4.00 |
| B | ALCOHOL | 6.00 |

Prophetic Example 2

Prophetic preparation of coacervate nanocapsules with hydrophilic microemulsified peptides containing just liquid lipids.

In a suitable vessel the following are added in this order: water, Amigel® [INCI: SCLEROTIUM GUM], hyaluronic acid [INCI: SODIUM HYALURONATE], Zemea® [INCI: PROPANEDIOL] and phenoxyethanol [INCI: PHENOXYETHANOL] (ingredients A), and the mixture is stirred until homogeneity is achieved.

In another vessel, the microemulsion of the corresponding peptide prepared according to example 1, soybean oil [INCI: GLYCINE SOJA (SOYBEAN) OIL], Arlacel™ 83 [INCI: SORBITAN SESQUIOLEATE], and Arlamol™ HD [INCI: ISOHEXADECANE] (ingredients B) are mixed.

Next, the mixture of ingredients B is added to the mixture of ingredients A, under stirring with a turbine until the emulsion is formed.

Finally, the mixture is homogenized under pressure in a microfluidizer for 3 cycles with an entrance pressure of 80 bar and pressure on exit of 15000 psi. Throughout the whole process the sample is kept at 25° C. by means of a water/glycol refrigerated circuit.

Next, a suspension of Quat Soy LDMA 25 [INCI: LAURYLDIMONIUM HYDROXYPROPYL HYDROLYZED SOY PROTEIN] (ingredients C) in water is added dropwise under stirring.

For the peptide H-Dpr-Ala-Asn-His-OH, the microemulsion prepared according to example 1-a is used.

| | INGREDIENT (INCI Nomenclature) | % IN WEIGHT |
|---|---|---|
| A | WATER (AQUA) | QSP100 |
| A | SCLEROTIUM GUM | 0.50 |
| A | PROPANEDIOL | 5.00 |
| A | PHENOXYETHANOL | 2.6 |
| A | SODIUM HYALURONATE | 0.01 |
| B | H-Dpr-Ala-Asn-His-OH, DIETHYLHEXYL SODIUM SULFOSUCCINATE/ISOSTEARIC ACID (15/85), WATER (AQUA), ALCOHOL | 8.00 |
| B | GLYCINE SOJA (SOYBEAN) OIL | 12.00 |
| B | SORBITAN SESQUIOLEATE | 4.30 |
| B | ISOHEXADECANE | 5.50 |
| C | WATER (AQUA) | 2.00 |
| C | LAURYLDIMONIUM HYDROXYPROPYL HYDROLYZED SOY PROTEIN | 0.20 |

The average size of the capsules in suspension obtained, containing the peptide H-Dpr-Ala-Asn-His-OH and determined by Dynamic Laser Light Scattering, is measured.

For the peptide Ac-Arg-Asn-His-Cit-NH$_2$, the microemulsion prepared according to example 1-b is used.

| | INGREDIENT (INCI Nomenclature) | % IN WEIGHT |
|---|---|---|
| A | WATER (AQUA) | QSP100 |
| A | SCLEROTIUM GUM | 0.50 |
| A | PROPANEDIOL | 5.00 |
| A | PHENOXYETHANOL | 2.6 |
| A | SODIUM HYALURONATE | 0.01 |
| B | Ac-Arg-Asn-His-Cit-NH$_2$, DIETHYLHEXYL SODIUM SULFOSUCCINATE/ISOSTEARIC ACID (15/85), WATER (AQUA), ALCOHOL | 10.00 |
| B | GLYCINE SOJA (SOYBEAN) OIL | 10.00 |
| B | SORBITAN SESQUIOLEATE | 6.50 |
| B | ISOHEXADECANE | 3.00 |
| C | WATER (AQUA) | 2.00 |
| C | LAURYLDIMONIUM HYDROXYPROPYL HYDROLYZED SOY PROTEIN | 0.20 |

The average size of the capsules in suspension obtained, containing the peptide Ac-Arg-Asn-His-Cit-NH$_2$ and determined by Dynamic Laser Light Scattering, is measured.

In the encapsulation of peptides, the separation of the encapsulated and non-encapsulated active ingredient is carried out by the basket centrifugation technique [David W. Fry et al. *Analytical Biochemistry* 90: 809-815 (1978)]. Once both fractions have been separated, the non-encapsulated part is analyzed by HPLC. It is expected that in no case peptide presence is detected in the aqueous phase of the dispersion, therefore, an encapsulation efficiency near 100% is expected.

Example 3

Preparation of microemulsions of hydrophilic actives for their subsequent encapsulation in coacervate nanocapsules which contain liquid lipids.

Example 3a. Microemulsion of the Peptide Ac-Glu-Glu-Met-Gln-Arg-Arg-Ala-NH$_2$ In a suitable vessel, the peptide Ac-Glu-Glu-Met-Gln-Arg-Arg-Ala-NH$_2$ [INCI: ACETYL HEPTAPEPTIDE-4] (phase A) was dissolved in water at 60° C. The solution was kept under stirring until room temperature was reached.

In another vessel, the following products were added following this order: soybean oil [INCI: SOYBEAN (*GLYCINE SOJA*) OIL], Abil® EM 90 [INCI: CETYL PEG/PPG-10/1 DIMETHICONE] and Span® 65 [INCI: SORBITAN TRISTEARATE] (phase B). The mixture was stirred and heated to 65° C.

Then, phase A at room temperature was added to phase B at 65° C., under stirring with a turbine until the microemulsion was formed. The mixture was kept under stirring until room temperature was reached.

|   | INGREDIENT (INCI Nomenclature) | % IN WEIGHT |
|---|---|---|
| A | WATER (AQUA) | 56.00 |
| A | ACETYL HEPTAPEPTIDE-4 | 2.00 |
| B | SOYBEAN (*GLYCINE SOJA*) OIL | 33.00 |
| B | CETYL PEG/PPG-10/1 DIMETHICONE | 5.00 |
| B | SORBITAN TRISTEARATE | 4.00 |

Example 3b. Microemulsion of the Peptide Diffuporine™

In a suitable vessel, the peptide Diffuporine™ [INCI: ACETYL HEXAPEPTIDE-37] (phase A) was dissolved in water at 60° C. The solution was kept under stirring until room temperature was reached.

In another vessel the following ingredients were added in this order: soybean oil [INCI: SOYBEAN (*GLYCINE SOJA*) OIL], Abil® EM 90 [INCI: CETYL PEG/PPG-10/1 DIMETHICONE] and Span® 65 [INCI: SORBITAN TRISTEARATE] (phase B). The mixture was stirred and heated to 65° C.

Then, phase A at room temperature was added to phase B at 65° C., under stirring with a turbine until the microemulsion was formed. The mixture was kept under stirring until room temperature was reached.

|   | INGREDIENT (INCI Nomenclature) | % IN WEIGHT |
|---|---|---|
| A | WATER (AQUA) | 55.83 |
| A | ACETYL HEXAPEPTIDE-37 | 0.17 |
| B | SOYBEAN (*GLYCINE SOJA*) OIL | 37.00 |
| B | CETYL PEG/PPG-10/1 DIMETHICONE | 5.00 |
| B | SORBITAN TRISTEARATE | 2.00 |

Example 3c. Microemulsion of Adenosine Triphosphate Disodium Salt

In a suitable vessel the following ingredients were added in this order: MgCl [INCI: MAGNESIUM CHLORIDE], Riboxyl™ [INCI: RIBOSE] and ADENOSINE TRIPHOSPHATE DISODIUM SALT (phase A) were dissolved in water. pH was adjusted at 7 using NaOH [INCI: SODIUM HYDROXIDE] (phase B).

In another vessel the following ingredients were added in this order: soybean oil [INCI: SOYBEAN (*GLYCINE SOJA*) OIL] and Lipochroman® [INCI: DIMETHYLMETHOXY CHROMANOL] (phase C). The solution was heated at 50° C. in order to dissolve Lipochroman®. Then, it was kept under stirring until room temperature was reached. At this point, Abil® EM 90 [INCI: CETYL PEG/PPG-10/1 DIMETHICONE] (phase D) was added.

Then, phase A+B was added to phase C+D, under stirring with a turbine until the microemulsion was formed.

|   | INGREDIENT (INCI Nomenclature) | % IN WEIGHT |
|---|---|---|
| A | MAGNESIUM CHLORIDE | 0.53 |
| A | RIBOSE | 10.00 |
| A | ADENOSINE TRIPHOSPHATE DISODIUM | 10.00 |
| C | SALT | 37.00 |
| C | SOYBEAN (*GLYCINE SOJA*) OIL | 0.83 |
| D | DIMETHYLMETHOXY CHROMANOL CETYL PEG/PPG-10/1 DIMETHICONE | 2.50 |
| A | WATER (AQUA) | 37.84 |
| B | SODIUM HYDROXIDE | 1.30 |

Example 4

Preparation of Coacervated Nanocapsules which Contain Liquid Lipids.

Example 4a. Preparation of Coacervated Nanocapsules Containing Liquid Lipids and with the Hydrophilic Microemulsified Peptide Ac-Glu-Glu-Met-Gln-Arg-Arg-Ala-NH$_2$ 1st Stage In a suitable vessel the following materials were added in this order: water [INCI: WATER (AQUA)], Zemea® [INCI: PROPANEDIOL], phenoxyethanol [INCI: PHENOXYETHANOL], Structure® XL [INCI: HYDROXYPROPYL STARCH PHOSPHATE], AMIGEL® [INCI: *SCLEROTIUM* GUM] and hyaluronic acid [INCI: SODIUM HYALURONATE] (phase A). The mixture was stirred until homogeneity was achieved. The mixture was heated to 65° C.

In another vessel, the following ingredients were added while stirring in this order: the microemulsion of the peptide prepared according to example 3a, Massocare™ HD [INCI: ISOHEXADECANE], Arlacelnu™ 83 [INCI: SORBITAN SESQUIOLEATE] and Lipochroman® [INCI: DIMETHYLMETHOXY CHROMANOL] (phase B). The mixture was heated to 65° C.

Then, phase B was added to phase A, under stirring with a turbine until an emulsion was formed.

Finally, the hot mixture was homogenized under pressure in a microfluidizer for 3 cycles with an entrance pressure of 80 bar and pressure on exit of 15000 psi. The mixture was kept under stirring until room temperature was reached.

|   | INGREDIENT (INCI Nomenclature) | % IN WEIGHT |
|---|---|---|
| A | WATER (AQUA) | QSP100 |
| A | PROPANEDIOL | 5.58 |
| A | PHENOXYETHANOL | 2.90 |
| A | HYDROXYPROPYL STARCH PHOSPHATE | 0.34 |

-continued

| | INGREDIENT (INCI Nomenclature) | % IN WEIGHT |
|---|---|---|
| A | *SCLEROTIUM* GUM | 0.11 |
| A | SODIUM HYALURONATE | 0.01 |
| B | Example 3a | 27.91 |
| B | ISOHEXADECANE | 5.58 |
| B | SORBITAN SESQUIOLEATE | 4.47 |
| B | DIMETHYLMETHOXY CHROMANOL | 0.06 |

2$^{nd}$ Stage

In a suitable vessel the following ingredients were added in this order: mixture obtained in the 1$^{st}$ stage of this example 4a (phase A), water [INCI: WATER (AQUA)] and Quat Soy LDMA 25 [INCI: LAURYLDIMONIUM HYDROXYPROPYL HYDROLYZED SOY PROTEIN] (phase B). The mixture was stirred until homogeneity was achieved and the nanocapsules coacervated with Quat Soy LDMA 25 and hyaluronic acid were obtained.

Then, Structure® XL [INCI: HYDROXYPROPYL STARCH PHOSPHATE] and Amigel® [INCI: *SCLEROTIUM* GUM] (phase C) were added under stirring until homogeneity.

Finally, Sepigel™ 305 [INCI: POLYACRYLAMIDE/WATER (AQUA)/C13-14 ISOPARAFFIN/LAURETH-7] (phase D) was added and the mixture was kept under stirring until complete homogenization.

| | INGREDIENT (INCI Nomenclature) | % IN WEIGHT |
|---|---|---|
| A | 1st stage of example 4a | 93.55 |
| B | WATER (AQUA) | 2.00 |
| B | LAURYLDIMONIUM HYDROXYPROPYL HYDROLYZED SOY PROTEIN | 0.20 |
| C | HYDROXYPROPYL STARCH PHOSPHATE | 1.50 |
| C | *SCLEROTIUM* GUM | 0.75 |
| D | POLYACRYLAMIDE/WATER (AQUA)/C13-14 ISOPARAFFIN/LAURETH-7 | 2.00 |

Example 4b. Preparation of Coacervated Nanocapsules Containing Liquid Lipids and the Hydrophilic Microemulsified Peptide Diffuporine™

1st Stage

In a suitable vessel the following ingredients were added in this order: water [INCI: WATER (AQUA)], Zemea® [INCI: PROPANEDIOL], phenoxyethanol [INCI: PHENOXYETHANOL], Structure® XL [INCI: HYDROXYPROPYL STARCH PHOSPHATE], Amigel® [INCI: *SCLEROTIUM* GUM] and hyaluronic acid [INCI: SODIUM HYALURONATE] (phase A). The mixture was stirred until homogeneity was achieved and it was heated to 65° C.

In another vessel, the following ingredients were added in this order: the microemulsion of the peptide prepared according to example 3b, Massocare™ HD [INCI: ISOHEXADECANE], Arlacel™ 83 [INCI: SORBITAN SESQUIOLEATE] and Lipochroman® [INCI: DIMETHYLMETHOXY CHROMANOL] (phase B) were mixed. The mixture was heated to 65°.

Then, phase B was added to phase A, under stirring with a turbine until an emulsion was formed.

Finally, the hot mixture was homogenized under pressure in a microfluidizer for 3 cycles with an entrance pressure of 80 bar and pressure on exit of 15000 psi. The mixture was kept under stirring until room temperature was reached.

| | INGREDIENT (INCI Nomenclature) | % IN WEIGHT |
|---|---|---|
| A | WATER (AQUA) | QSP100 |
| A | PROPANEDIOL | 5.00 |
| A | PHENOXYETHANOL | 2.60 |
| A | HYDROXYPROPYL STARCH PHOSPHATE | 1.00 |
| A | *SCLEROTIUM* GUM | 0.50 |
| A | SODIUM HYALURONATE | 0.01 |
| B | Example 3B | 30.00 |
| B | ISOHEXADECANE | 5.00 |
| B | SORBITAN SESQUIOLEATE | 4.00 |
| B | DIMETHYLMETHOXY CHROMANOL | 0.05 |

2$^{nd}$ Stage

In a suitable vessel the following ingredients were added in this order: mixture obtained in the 1$^{st}$ stage of this example 4b (phase A), water [INCI: WATER (AQUA)] and Quat Soy LDMA 25 [INCI: LAURYLDIMONIUM HYDROXYPROPYL HYDROLYZED SOY PROTEIN] (phase B). The mixture was stirred until homogeneity was achieved and the nanocapsules coacervated with Quat Soy LDMA 25 and hyaluronic acid were obtained.

Then, Structure® XL [INCI: HYDROXYPROPYL STARCH PHOSPHATE] and Amigel® [INCI: *SCLEROTIUM* GUM] (phase C) were added under stirring until homogeneity.

| | INGREDIENT (INCI Nomenclature) | % IN WEIGHT |
|---|---|---|
| A | 1st stage of example 4b | 91.55 |
| B | WATER (AQUA) | 6.00 |
| B | LAURYLDIMONIUM HYDROXYPROPYL HYDROLYZED SOY PROTEIN | 0.20 |
| C | HYDROXYPROPYL STARCH PHOSPHATE | 1.50 |
| C | *SCLEROTIUM* GUM | 0.75 |

The average size of the capsules obtained, containing the Diffuporine™ peptide and determined by Dynamic Laser Light Scattering, was 192 nm.

The separation of the encapsulated and non-encapsulated Diffuporine™ peptide was carried out by the basket centrifugation technique [David W. Fry et al. *Analytical Biochemistry* 90: 809-815 (1978)]. Once both fractions had been separated, the non-encapsulated part was analyzed by HPLC. No Diffuporine™ peptide presence was detected in the aqueous phase of the dispersion, therefore, an encapsulation efficiency of 100% was obtained.

The stability of Diffuporine™ peptide in the coacervated nanocapsules was measured at time 0 hours, 1 month at room temperature and 1 month at 40° C. 100% of Diffuporine™ peptide regarding the initial amount of peptide was found at time 0 hours after the formation of the coacervated nanocapsules. Therefore, the peptide was stable during the preparation process of the coacervated nanocapsules. 100% of the peptide regarding the initial amount was also found after 1 month at room temperature or after 1 month at 40° C.

Example 4c. Preparation of Coacervated Nanocapsules Containing Liquid Lipids and the Hydrophilic Microemulsified Active Adenosine Triphosphate Disodium 1st Stage In a suitable vessel the following ingredients were added in this order: water [INCI: WATER (AQUA)], Riboxyl™ [INCI: RIBOSE], Zemea® [INCI: PROPANEDIOL], phenoxyethanol [INCI: PHENOXYETHANOL], Structure® XL [INCI: HYDROXYPROPYL STARCH PHOSPHATE], Amigel® [INCI: *SCLEROTIUM* GUM] and hyaluronic acid [INCI: SODIUM HYALURONATE] (phase A). The mixture was stirred until homogeneity was achieved.

In another vessel, the following ingredients were added in this order: the microemulsion of the corresponding compound prepared according to example 1c, Massocare™ HD [INCI: ISOHEXADECANE], and polysorbate 20 [INCI: POLYSORBATE 20] (phase B) were mixed.

Then, phase B was added to phase A, under stirring with a turbine until the emulsion was formed.

Finally, the mixture was homogenized under pressure in a microfluidizer for 3 cycles with an entrance pressure of 80 bar and pressure on exit of 15000 psi.

|   | INGREDIENT (INCI Nomenclature) | % IN WEIGHT |
|---|---|---|
| A | WATER (AQUA) | QSP100 |
| A | RIBOSE | 4.28 |
| A | PROPANEDIOL | 5.34 |
| A | PHENOXYETHANOL | 2.78 |
| A | HYDROXYPROPYL STARCH PHOSPHATE | 1.07 |
| A | *SCLEROTIUM* GUM | 0.53 |
| A | SODIUM HYALURONATE | 0.01 |
| B | Example 1C | 10.69 |
| B | ISOHEXADECANE | 5.34 |
| B | POLYSORBATE 20 | 4.28 |

$2^{nd}$ Stage

In a suitable vessel the following ingredients were added in this order: mixture obtained in the $1^{st}$ stage of this example 4c (phase A), water [INCI: WATER (AQUA)] and Quat Soy LDMA 25 [INCI: LAURYLDIMONIUM HYDROXYPROPYL HYDROLYZED SOY PROTEIN] (phase B) were mixed and the mixture was stirred until homogeneity was achieved and the coacervated nanocapsules were obtained.

Then, Structure® XL [INCI: HYDROXYPROPYL STARCH PHOSPHATE], Amigel® [INCI: *SCLEROTIUM* GUM] (phase C) were added under stirring until homogeneity.

Finally, Sepigel™ 305 [INCI: POLYACRYLAMIDE/ WATER (AQUA)/C13-14 ISOPARAFFIN/LAURETH-7] (phase D) was added and the mixture was kept under stirring until complete homogenization.

|   | INGREDIENT (INCI Nomenclature) | % IN WEIGHT |
|---|---|---|
| A | 1st stage of this example 2c | 93.55 |
| B | WATER (AQUA) | 2.00 |
| B | LAURYLDIMONIUM HYDROXYPROPYL HYDROLYZED SOY PROTEIN | 0.20 |
| C | HYDROXYPROPYL STARCH PHOSPHATE | 1.50 |
| C | *SCLEROTIUM* GUM | 0.75 |
| D | POLYACRYLAMIDE/WATER (AQUA)/C13-14 ISOPARAFFIN/LAURETH-7 | 2.00 |

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. Polymerically coated nanocapsules, each comprising:
a water-in-liquid lipids microemulsion comprising: liquid lipids water, and at least one hydrophilic active ingredient, the microemulsion including an internal aqueous phase, which includes the at least one hydrophilic active ingredient dissolved therein, the internal aqueous phase being incorporated, as drops, in the liquid lipids, by homogenization, the at least one hydrophilic active ingredient comprising a peptide, and
a polymeric coating, which encapsulates the microemulsion to provide a complete and continuous coating of the microemulsion,
wherein the polymeric coating is a complex coacervate formed from first and second polymers by complex coacervation, without crosslinking,
wherein the nanocapsules have an average size, as determined by dynamic laser light scattering, of 50 nm to 1000 nm, and
wherein the drops of the nanocapsules have a size which ranges between 10 nm and 20 nm.

2. The nanocapsules according to claim 1, wherein the liquid lipids are selected from the group consisting of vegetable oils, soybean oil, sunflower oil, corn oil, olive oil, palm oil, cottonseed oil, colza oil, peanut oil, coconut oil, castor oil, linseed oil, borage oil, evening primrose oil, marine oils, fish oils, algae oils, oils derived from petroleum, mineral oil, liquid paraffin, vaseline, short-chain fatty alcohols, medium-chain aliphatic branched fatty alcohols, fatty acid esters with short-chain alcohols, isopropyl myristate, isopropyl palmitate, isopropyl stearate, dibutyl adipate, medium-chain triglycerides, capric and caprylic triglycerides, $C_{12}$-$C_{16}$ octanoates, fatty alcohol ethers, dioctyl ether, and mixtures thereof.

3. The nanocapsules according to claim 1, wherein the first and second polymers of the coating are selected from the group consisting of proteins, polysaccharides, polyesters, polyacrylates, polycyanoacrylates, copolymers, and mixtures thereof.

4. The nanocapsules according to claim 3, wherein the first and second polymers of the coating are selected from the group consisting of gelatin, albumin, soy protein, pea protein, broad bean protein, potato protein, wheat protein, whey protein, β-lactoglobulin, caseinates, zein, alginates, carrageenans, pectins, gum arabic, xanthan gum, guar gum, chitosan, poly(L-lysine), dextran sulfate sodium, carboxymethyl galactomannan, carboxymethyl cellulose, cellulose nitrate, cellulose acetate phthalate, cellulose hydroxypropyl methyl phthalate, cellulose hydroxypropyl methyl acetate succinate, polyvinyl acetate phthalate, and mixtures thereof.

5. The nanocapsules according to claim 1, wherein one of the first and second the polymers of the coating is a cationic polymer.

6. The nanocapsules according to claim 5, wherein the cationic polymer is selected from the group consisting of cationic derivatives of cellulose, quaternized hydroxyethyl cellulose, cationic starches, diallyl ammonium and acrylamide salt copolymers; quaternized vinylpyrrolidone/vinylimidazole polymers, condensation products of polyglycols and amines, polyquaternium polymers and copolymers, polymers of polyquaternium-6, polyquaternium-7, polyquaternium-16, polyquaternium-10, polyquaternium-4 copolymers, dicocoylethylhydroxyethylammonium, graft copolymers with a cellulose skeleton and quaternary ammonium groups; quaternized collagen polypeptides, lauryldimonium hydroxypropyl hydrolyzed collagen, quaternized wheat polypeptides, polyethylenimine, cationic silicone polymers, amidomethicone or quaternium-22 silicone, adipic acid and dimethylamino hydroxypropyl diethylenetriamine copolymers, acrylic acid copolymers with dimethyldiallylammonium chloride, cationic chitin derivatives, chitosan and its derivatives, condensation products of cationic dihalogen alkylene, condensation products of dibromobutane with bisdialkylamines, bis-dimethylamino-1,3-propane, derivatives of cationic guar gum, guar-hydroxypropyltrimonium, quaternary ammonium salt polymers, quaternized polysaccharide polymers of natural derivatives such as azarose, cationic proteins of gelatin, cationic proteins of gum arabic, cationic polymers of polyamides, cationic polymers of polycyanoacrylates, cationic polymers of polylactides, cationic polymers of polyglycolides, cationic polymers of polyaniline, cationic polymers of polypyrrole, cationic polymers of polyvinylpyrrolidone, cationic polymers of amino silicone polymers and copolymers, cationic polymers of polystyrene, cationic polymers of polyvinyl alcohol, cationic polymers of polystyrene and maleic acid anhydride copolymers, cationic polymers of methyl vinyl ether, cationic polymers of epoxy resins, cationic polymers of styrene and methyl methacrylate copolymers, cationic dimethylamino methacrylate, polyacrylates and polymethacrylates, polyamine derivatives optionally substituted by polyethylene glycol derivatives, polyamino acids under pH conditions wherein they are cationic, polyethyleneimine; quaternized derivatives of polyvinylpyrrolidone and hydrophilic urethane polymers, and mixtures thereof.

7. The nanocapsules according to claim 1, wherein the hydrophilic active ingredient further comprises a hydrophilic active ingredient which is selected from the group consisting of amino acids, proteins, enzymes, hormones, vitamins, mineral salts, sugars, nucleotides, nucleic acids, molecules or extracts of biological and biotechnological origin, vaccines, synthetic or partially synthetic hydrophilic molecules, and mixtures thereof.

8. The nanocapsules according to claim 1, further comprising other cosmetic, pharmaceutical and/or alimentary active ingredients and/or adjuvants.

9. The nanocapsules according to claim 8, wherein the other cosmetic and/or alimentary active ingredients and/or adjuvants are selected from the group consisting of surfactants, humectants or substances which retain moisture, moisturizers or emollients, agents stimulating healing, coadjuvant healing agents, agents stimulating re-epithelialization, coadjuvant re-epithelialization agents, agents which synthesize dermal or epidermal macromolecules, firming and/or redensifying and/or restructuring agents, cytokine growth factors, agents which act on capillary circulation and/or microcirculation, anti-glycation agents, free radical scavengers and/or anti-atmospheric pollution agents, reactive carbonyl species scavengers, 5α-reductase-inhibiting agents, lysyl- and/or prolyl hydroxylase inhibiting agents, defensin synthesis-stimulating agents, bactericidal agents and/or bacteriostatic agents and/or antimicrobial agents and/or germicidal agents and/or fungicidal agents and/or fungistatic agents and/or germ-inhibiting agents, anti-viral agents, antiparasitic agents, antihistaminic agents, nitric oxide-synthase inhibiting agents, desquamating agents or keratolytic agents and/or exfoliating agents, comedolytic agents, anti-psoriasis agents, anti-dandruff agents, anti-inflammatory agents and/or analgesics, anesthetic agents, anti-wrinkle and/or anti-aging agents, cosmetic and/or absorbent and/or body odor masking deodorants, antiperspirant agents, perfuming substances and/or perfumed oils and/or isolated aromatic compounds, anti-oxidizing agents, agents inhibiting vascular permeability, hydrolytic epidermal enzymes, whitening or skin depigmenting agents, agents inhibiting sweat-degrading enzymes, agents capable of filtering UV rays, agents which stimulate or regulate keratinocyte differentiation, anti-itching agents, agents which stimulate or inhibit the synthesis of melanin, propigmenting agents, self-tanning agents, melanocyte proliferation stimulating agent, liquid propellants, vitamins, amino acids, proteins, biopolymers, gelling polymers, skin relaxant agents, agents capable of reducing or treating bags under eyes, agents for the treatment and/or care of sensitive skin, astringent agents, agents regulating sebum production, anti-stretch mark agents, lipolytic agents or agents stimulating lipolysis, venotonic agents, anti-cellulite agents, calming agents, agents acting on cell metabolism, agents to improve dermal-epidermal junction, agents inducing hair growth or hair-loss retardants, body hair growth inhibiting or retardant agents, heat shock protein synthesis stimulating agents, muscle relaxants, muscle contraction inhibitory agents, agents inhibiting acetylcholine receptor clustering, anticholinergic agents, elastase inhibitory agents, matrix metalloproteinase inhibitory agents, chelating agents, vegetable extracts, essential oils, marine extracts, mineral salts, cell extracts, emulsifying agents, agents stimulating the synthesis of lipids and components of the stratum corneum, ceramides, fatty acids, agents obtained from a bio-fermentation process and/or mixtures thereof.

10. The nanocapsules according to claim 8, wherein the other pharmaceutical active ingredients and/or adjuvants are selected from the group consisting of antiacids, agents against peptic ulcers and gastroesophageal reflux disease, antispasmodics, analgesics, anticholinergic drugs, propulsive drugs, antiemetics, antinausea drugs, agents for biliary therapy, agents for hepatic therapy, lipotropics, laxatives, antidiarrhetics, intestinal adsorbents, antipropulsives, anti-inflammatory drugs, active ingredients against obesity, enzymes, hypoglycemic drugs, insulin and analogues, vitamins, proteins, minerals, anabolic steroids, antithrombotic agents, antifibrinolytics, haemostatic agents, antiarrhythmic agents, cardiac stimulants, cardiac glycosides, vasodilators, antiadrenergic agents, antihypertensive drugs, diuretics, potassium-saving agents, antihemorrhoidals, antivaricose therapy agents, capillary stabilizing agents, agents which act on the renin-angiotensin system, beta-blockers, selective calcium-channel blockers, non-selective calcium-channel blockers, angiotensin-converting-enzyme inhibitors, angiotensin II inhibitors, agents modifying lipids, antifungals, healing agents, antipruritics, antihistamines, anesthetics, antipsoriatics, chemotherapy drugs, corticosteroids, antiseptics, disinfectants, anti-acne agents, products for gynecological use, oxytocics, anticonceptives, androgen, estrogen, progestagen, ovulation stimulants, gonadotropins, antiandrogens, products for urological use, antispasmodics, drugs used in benign prostatic hypertrophy, hormones, hormone antagonists, antibiotics, tetracyclines, anphenicols, beta-lactam antibacterials, penicillin, sulfonamides, trimethoprim, macrolides, lincosam ides, streptogram ins, antibacterial am inoglycosides, antibacterial quinolones, antivirals, immune serum, immunoglobulins, antineoplastic agents, immunomodulatory agents, alkylation agents, antimetabolites, plant alkaloids and other natural products, cytotoxic antibiotics, immunosuppressive agents, drugs for disorders of the musculoskeletal system, antirheumatics, muscle relaxant agents, agents which affect bone structure and mineralization, drugs which act on the nervous system, general anesthetics, local anesthetics, opioids, antimigraine agents, anticonvulsants, anticholinergic agents, dopaminergic agents, antipsychotics, anxiolytics, hypnotics, sedatives, antidepressants, psychostimulants, anti-dementia drugs, parasympathomimetics, drugs used in addictive disorders, anti-vertigo agents, antiparasitic agents, insecticides, insect repellants, nasal decongestants, mucolytic agents, cough suppressants, ophthalmic active ingredients, otological active ingredients, antiglaucoma drugs, miotics, mydriatics, cycloplegics, and mixtures thereof.

11. A cosmetic, pharmaceutical and/or alimentary composition which comprises the nanocapsules according to claim 1.

12. The composition according to claim 11, wherein the nanocapsules are adsorbed onto a solid organic polymer or solid mineral support selected from the group consisting of talc, bentonite, silica, starch, and maltodextrin.

13. The composition according to claim 11, wherein this composition is present in a formulation selected from the group consisting of creams, multiple emulsions, anhydrous compositions, aqueous dispersions, oils, milks, balsams, foams, lotions, gels, cream gels, hydroalcoholic solutions, hydroglycolic solutions, hydrogels, liniments, sera, soaps, shampoos, conditioners, serums, ointments, mousses, pomades, powders, bars, pencils, vaporizers, aerosols, capsules, gelatin capsules, soft capsules, hard capsules, tablets, sugar coated tablets, granules, chewing gum, solutions, suspensions, emulsions, syrups, polysaccharide films, jellies, and gelatin.

14. The composition according to claim 11, wherein the composition is incorporated into a product selected from the group consisting of under-eye concealers, make-up foundation, make-up removal lotions, make-up removal milks, eye shadows, lipsticks, lip gloss, lip protectors, and powders.

15. The composition according to claim 11, wherein the nanocapsules are incorporated into a woven fabric, a non-woven fabric or a medical device.

16. The nanocapsules according to claim 1, wherein the first polymer is a protein and the second polymer is a polysaccharide.

17. The nanocapsules according to claim 16, wherein the complex coacervate is a complex coacervate of soy protein and carboxymethyl cellulose.

18. The nanocapsules according to claim 1, wherein the at least one hydrophilic active ingredient includes a peptide selected from dipeptide-4, tripeptide-1, tripeptide-2, pentapeptide-3, pentapeptide, pentapeptide-18, hexapeptide-9, heptapeptide, nonapeptide-1, tripeptide-9 citrulline, tripeptide-10 citrulline, tripeptide-30 citrulline, hexapeptide-10, acetyl dipeptide-1, acetyl tetrapeptide-2, acetyl tetrapeptide-9, acetyl tetrapeptide-11, acetyl tetrapeptide-15, acetyl hexapeptide-1, acetyl heptapeptide-1, acetyl tripeptide-10 citrulline, acetyl tripeptide-40, acetyl tetrapeptide-22, acetyl hexapeptide, acetyl hexapeptide-8, acetyl hexapeptide-30, acetyl heptapeptide-4, acetyl octapeptide-3, trifluoroacetyl tripeptide-2, acetyl-glutamyl-methionyl-alanyl-isoleucine, acetyl-arginyl-phenylglycyl-phenylglycine, acetyl dipeptide-3 aminohexanoate, acetylarginyltriptophyl diphenylglycine, acetyl-arginyl-phenylglycyl-valyl-glycine, acetyl-arginyl-phenylglycyl-valyl-phenylglycine, diaminopropionyl-alanyl-asparaginyl-histidine, acetyl-arginyl-asparaginyl-histidyl-citrulline-am ideacetyl tetrapeptide-5, diaminopropionoyl tripeptide-33, palmitoyl tripeptide, palmitoyl tripeptide-5, palmitoyl tripeptide-8, palmitoyl tetrapeptide-7, palmitoyl pentapeptide-4, palmitoyl hexapeptide-19, palmitoyl oligopeptide, human oligopeptide-20, butiryl pentapeptide, tea-hydroiodide, caprooyl tetrapeptide-3, dipeptide diaminobutyroyl benzylamide diacetate, glutathione, carnosine, glucagon, leuprolide, goserelin, triptorelin, buserelin, nafarelin, deslorelin, histrelin, avorelin, abarelix, cetrorelix, ganirelix, degarelix, desmopressin, somatostatin octreotide, vapreotide, lanreotide, and mixtures thereof.

19. The nanocapsules of claim 1, wherein the nanocapsules are formed by a method comprising:
  a) preparing a water-in-liquid lipids microemulsion of an aqueous solution of the at least one hydrophilic active ingredient in the liquid lipids, and
  b) thereafter, encapsulating of the microemulsion with the polymeric coating.

20. The nanocapsules of claim 5, wherein one of the first and second polymers is quaternized soy protein.

21. The nanocapsules of claim 20, wherein the other of the first and second polymers is hyaluronic acid or a salt thereof.

* * * * *